(12) United States Patent
Johnson et al.

(10) Patent No.: US 12,279,842 B2
(45) Date of Patent: Apr. 22, 2025

(54) SURGICAL TOOL END EFFECTORS WITH DISTAL WEDGE SLOT CONSTRAINT

(71) Applicant: Cilag GmbH International, Zug (CH)

(72) Inventors: Eric Johnson, Maineville, OH (US); Jason Alan Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 677 days.

(21) Appl. No.: 17/518,273

(22) Filed: Nov. 3, 2021

(65) Prior Publication Data
US 2023/0135824 A1    May 4, 2023

(51) Int. Cl.
*A61B 34/37*    (2016.01)
*A61B 17/00*    (2006.01)
*A61B 34/00*    (2016.01)
*A61B 34/30*    (2016.01)

(52) U.S. Cl.
CPC ........ *A61B 34/37* (2016.02); *A61B 17/00234* (2013.01); *A61B 34/71* (2016.02); *A61B 2017/00327* (2013.01); *A61B 2034/301* (2016.02); *A61B 2034/305* (2016.02)

(58) Field of Classification Search
CPC ........ A61B 2034/301; A61B 2034/305; A61B 2017/00327; A61B 34/37; A61B 34/71
See application file for complete search history.

(56) References Cited

U.S. PATENT DOCUMENTS

| 6,840,938 | B1 * | 1/2005 | Morley | A61B 34/71 |
| | | | | 901/29 |
| 2007/0027469 | A1 * | 2/2007 | Smith | A61B 17/068 |
| | | | | 606/205 |
| 2010/0004663 | A1 * | 1/2010 | Murphy | A61B 34/30 |
| | | | | 606/130 |
| 2014/0148807 | A1 | 5/2014 | Kendrick | |
| 2018/0317915 | A1 * | 11/2018 | McDonald, II | A61B 17/07207 |
| 2019/0374241 | A1 | 12/2019 | Kapsdia | |
| 2021/0177495 | A1 | 6/2021 | Ross et al. | |
| 2022/0226050 | A1 | 7/2022 | Johnson et al. | |
| 2022/0338891 | A1 | 10/2022 | Johnson et al. | |

OTHER PUBLICATIONS

Written Opinion and International Search Report from corresponding PCT Application No. PCT/IB2022/060472 mailed Jan. 27, 2023.

* cited by examiner

*Primary Examiner* — Alyssa M Alter
*Assistant Examiner* — Jessandra F Hough
(74) *Attorney, Agent, or Firm* — Vorys, Sater, Seymour and Pease LLP

(57) ABSTRACT

A robotic surgical tool an elongate shaft, an end effector arranged at a distal end of the shaft and including opposing first and second jaws, and an articulable wrist interposing the end effector and the distal end of the shaft. The wrist includes a linkage mounted to the first and second jaws and defining a slot, a distal wedge positioned within a central portion of the wrist and providing a channel, and an alignment arm interposing the linkage and the distal wedge and providing an alignment head receivable within the slot and a projection receivable within the channel. The alignment head is translatable within the slot and the projection is translatable within the channel during operation of the end effector.

20 Claims, 20 Drawing Sheets

SURGICAL TOOL END EFFECTORS WITH DISTAL WEDGE SLOT CONSTRAINT

TECHNICAL FIELD

The systems and methods disclosed herein are directed to robotic surgical tools and, more particularly to, surgical tool end effectors that provide distal wedge slot constraint that limits unwanted jaw rotations with respect to a distal articulation joint, and thereby reduces jaw backlash.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Improvements to robotically-enabled medical systems will provide physicians with the ability to perform endoscopic and laparoscopic procedures more effectively and with improved ease.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
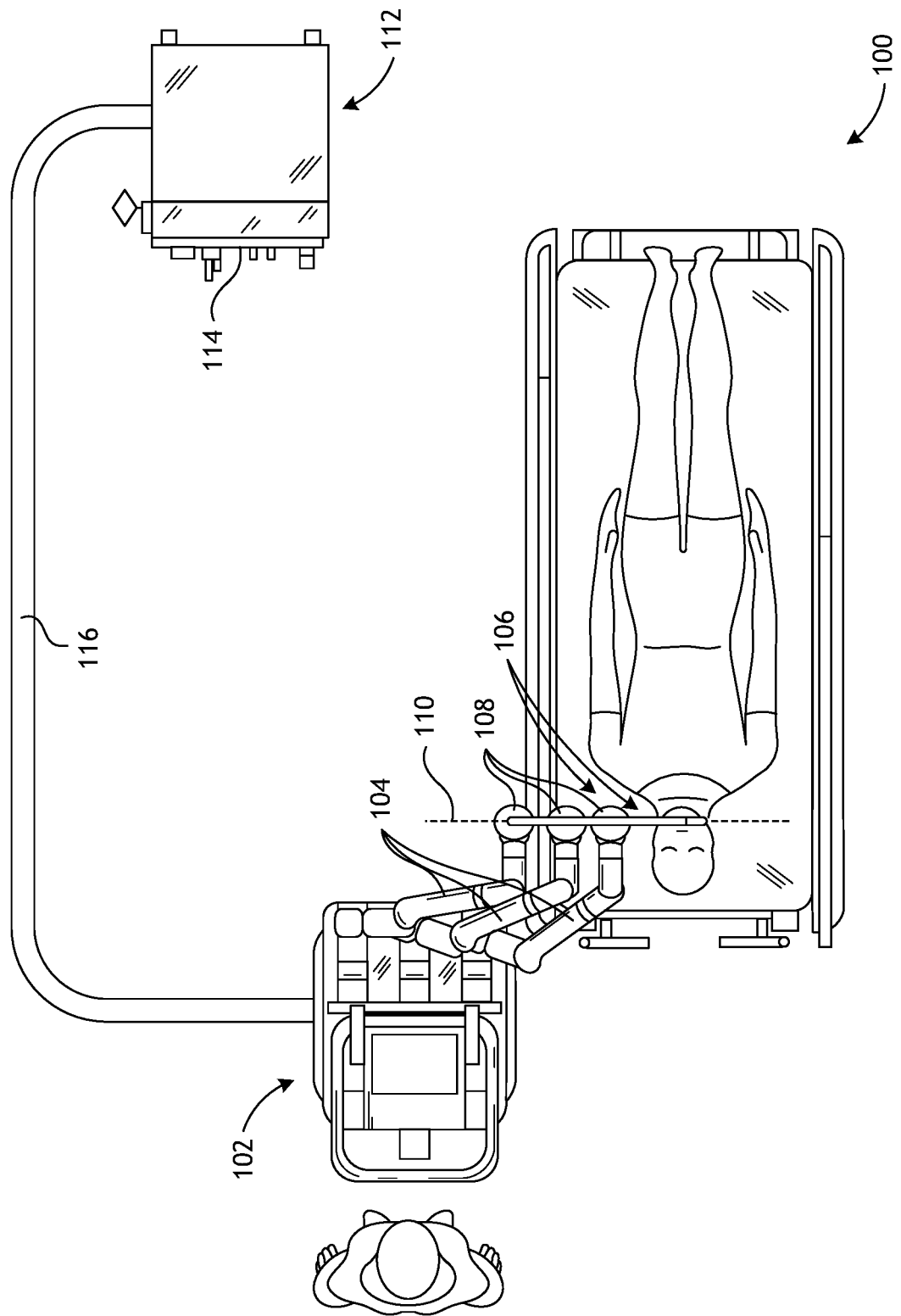
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastrointestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
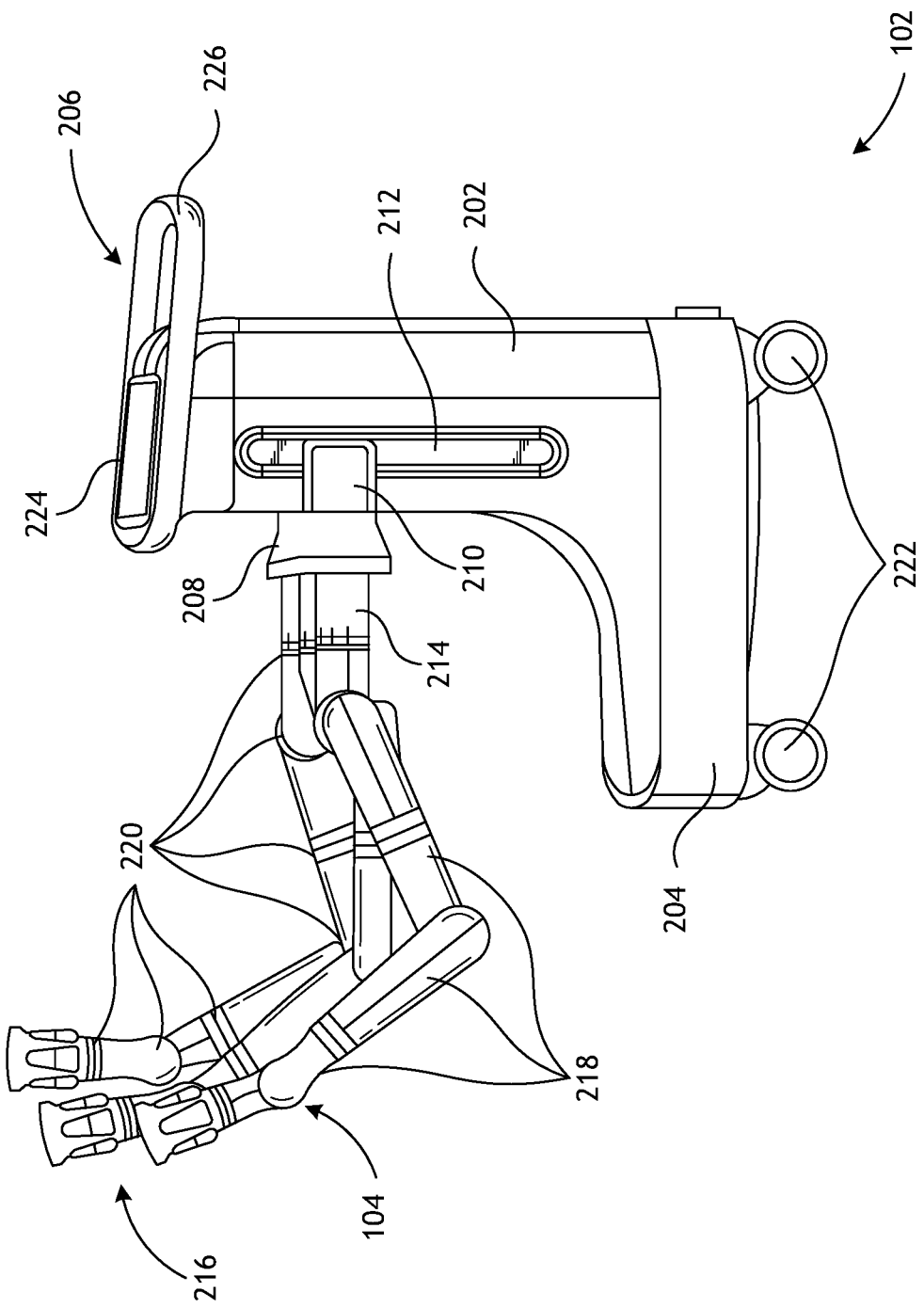
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
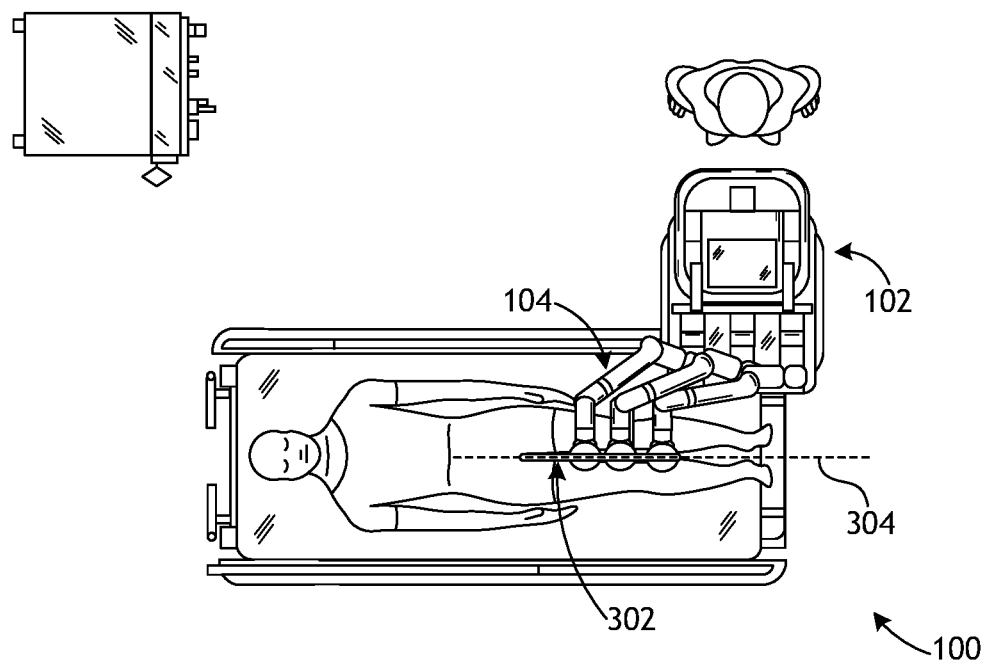
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
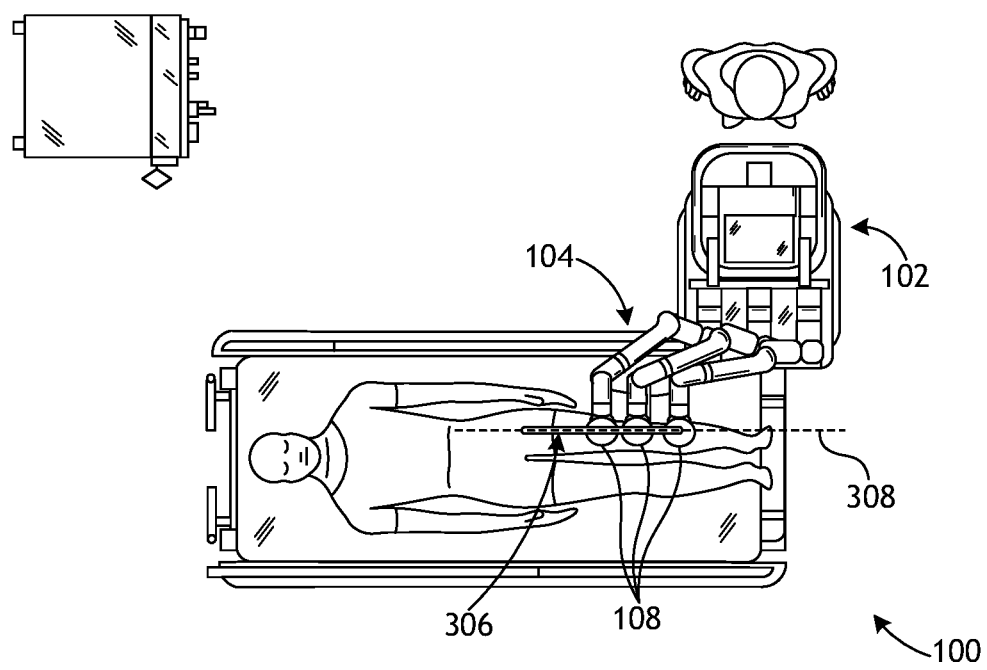
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
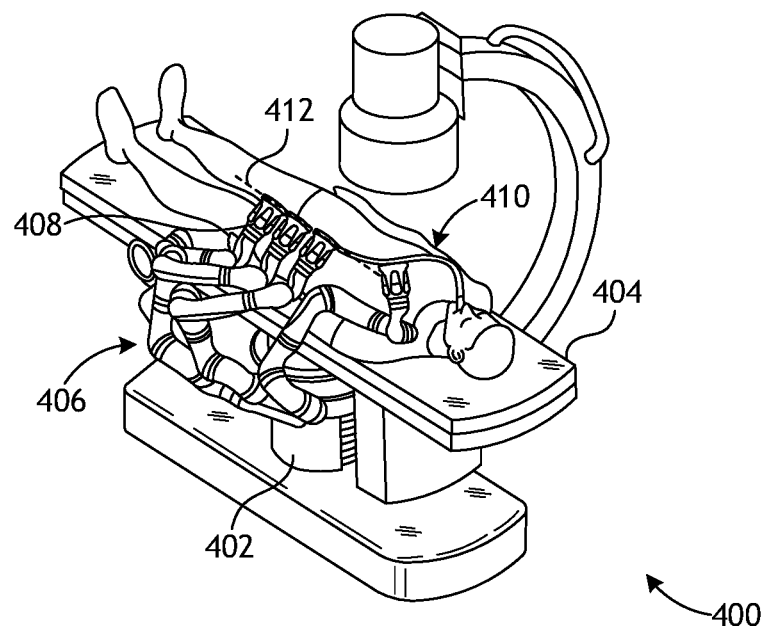
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
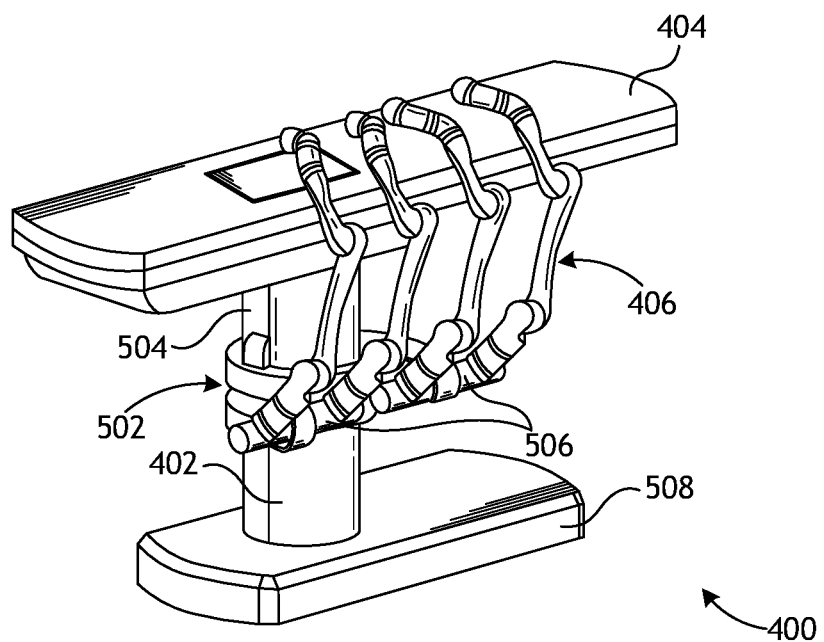
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
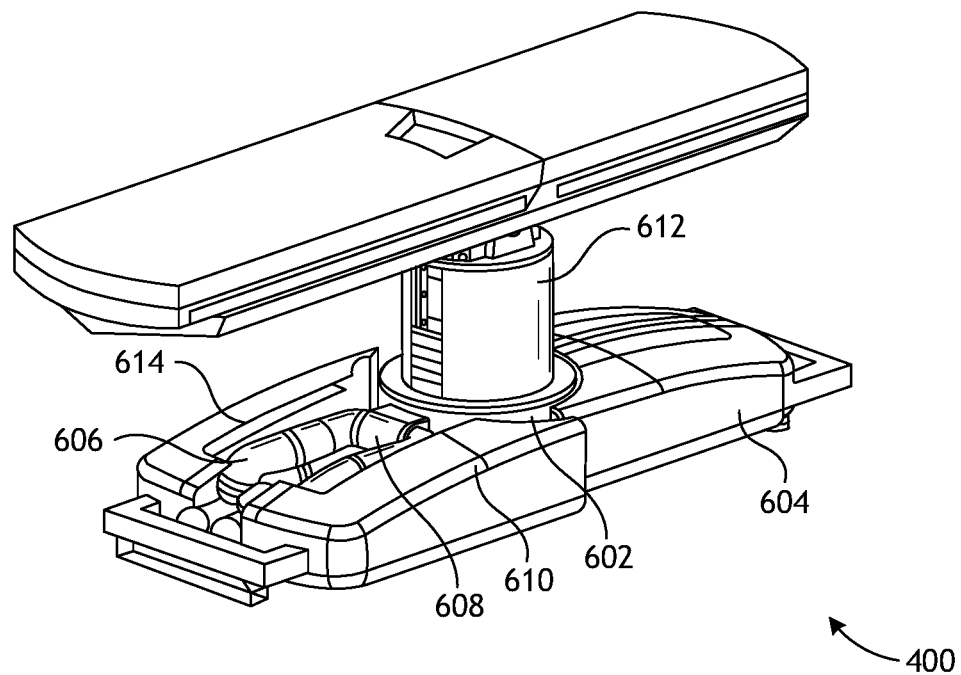
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
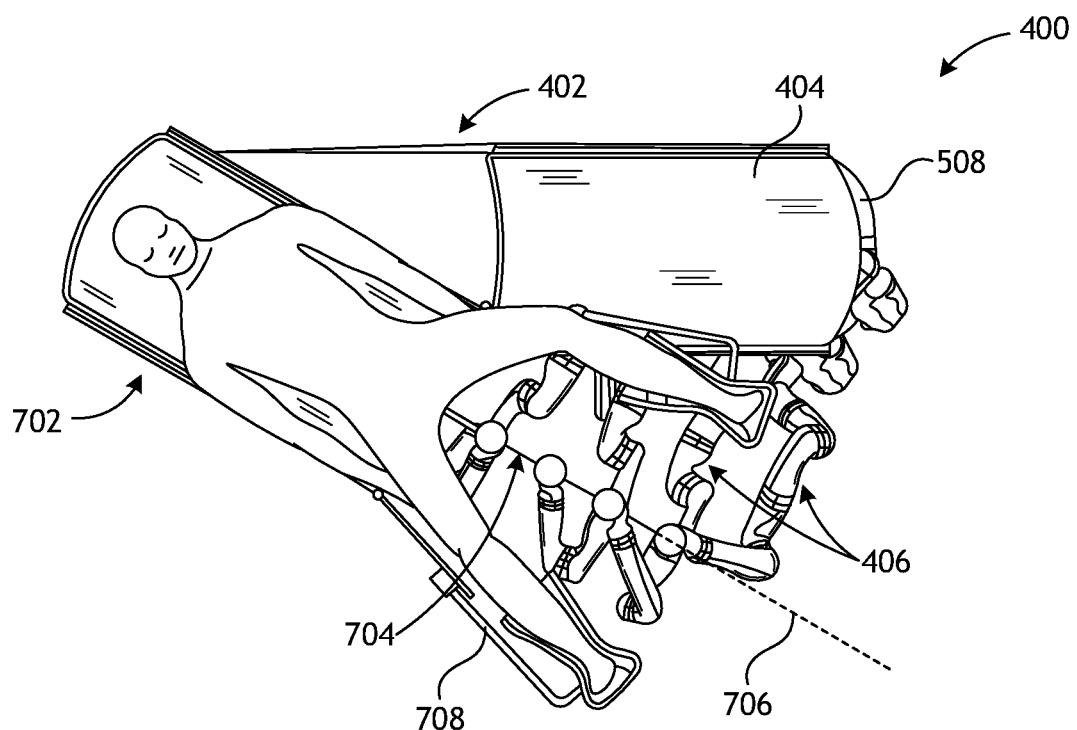
FIG. 7A illustrates an embodiment of a table-based robotic system configured for a ureteroscopy procedure.
Figure 7B:
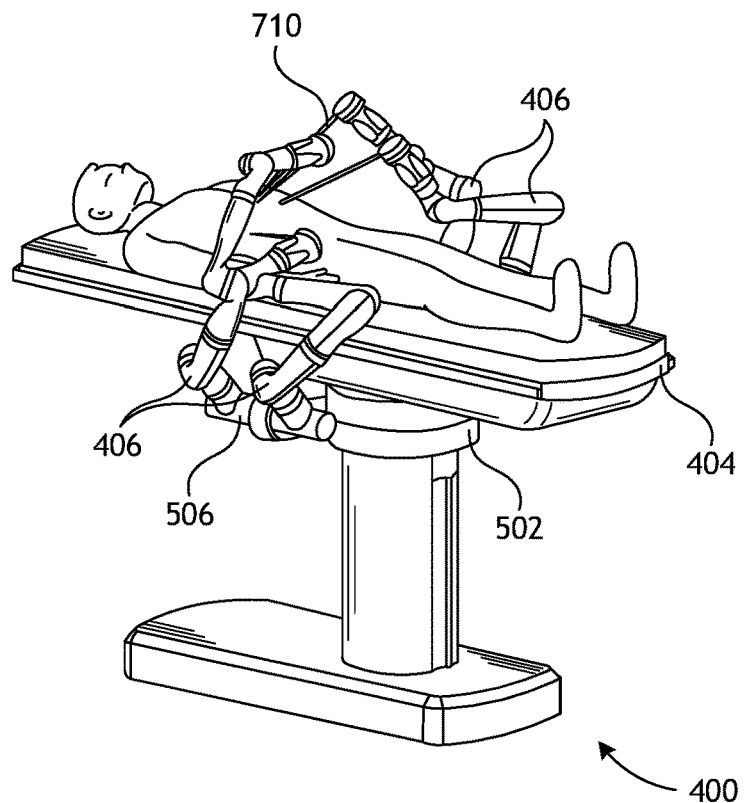
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
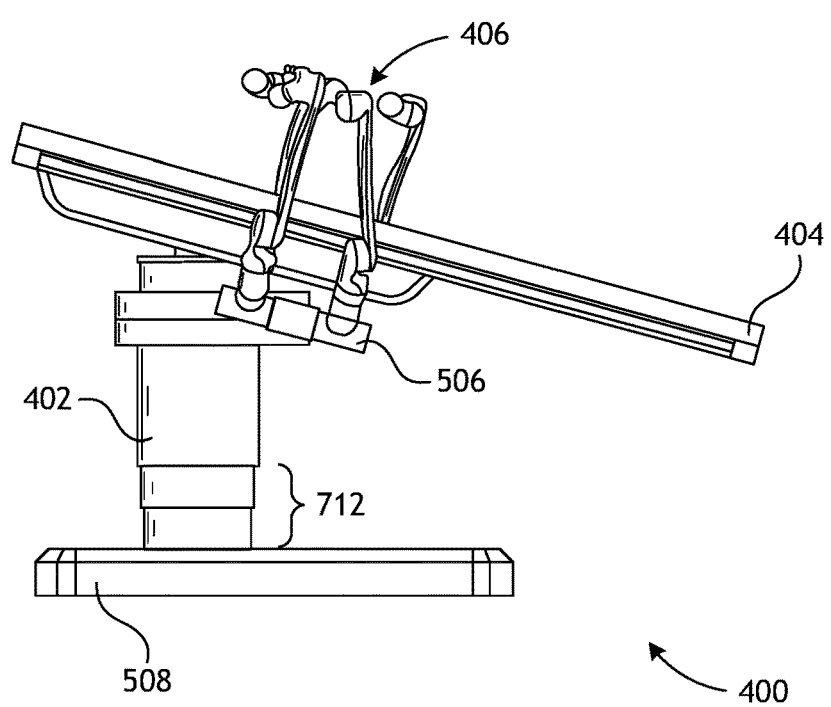
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
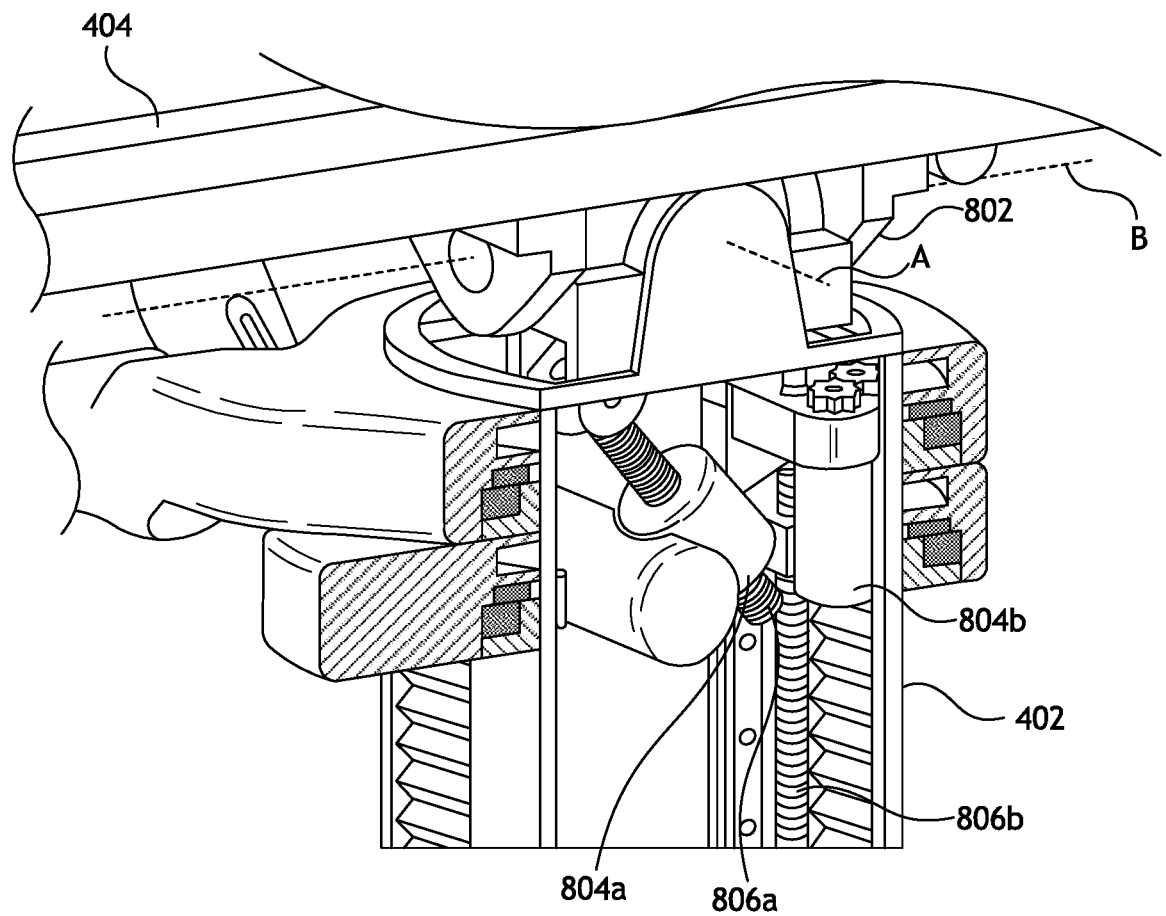
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
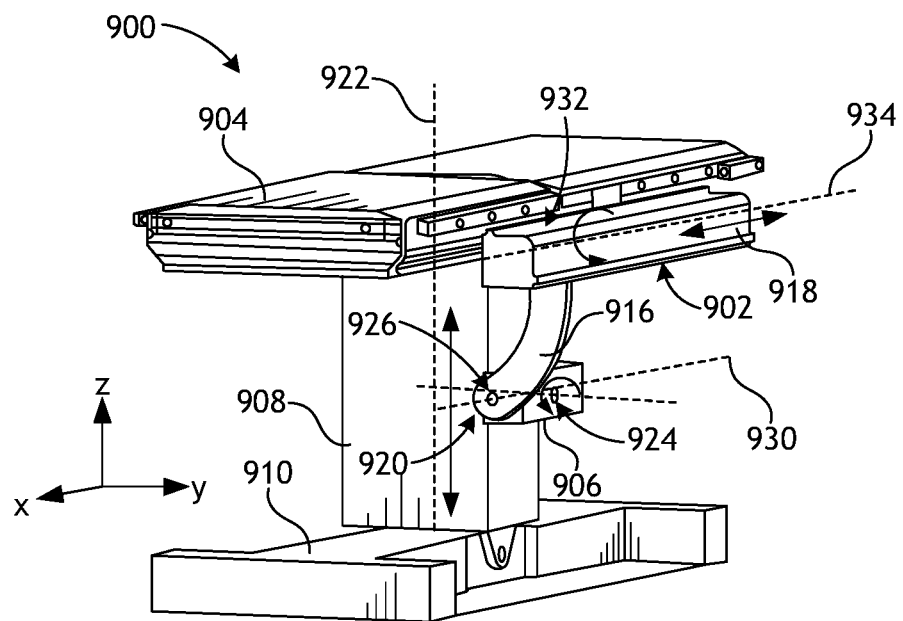
FIG. 9A illustrates an alternative embodiment of a table-based robotic system.
Figure 9B:
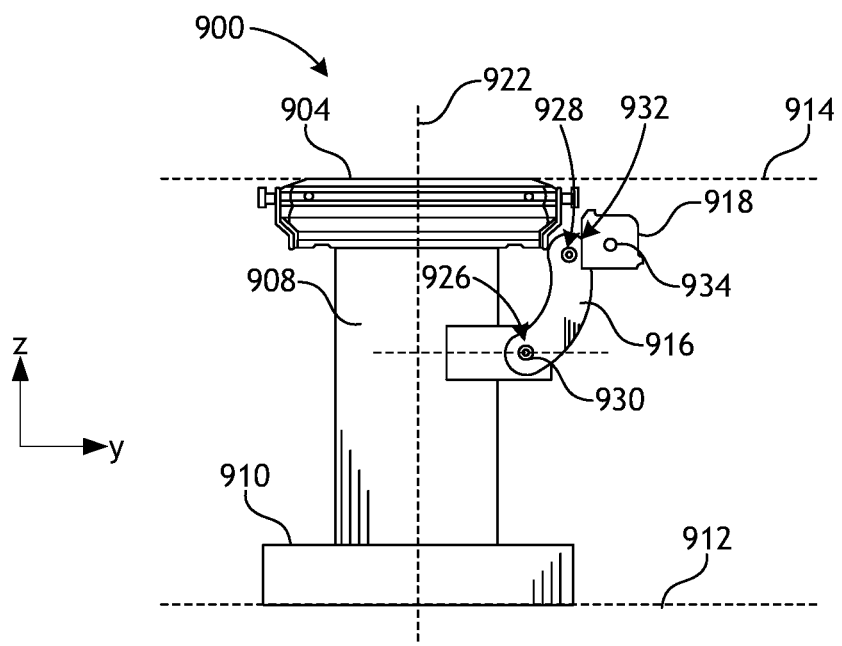
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
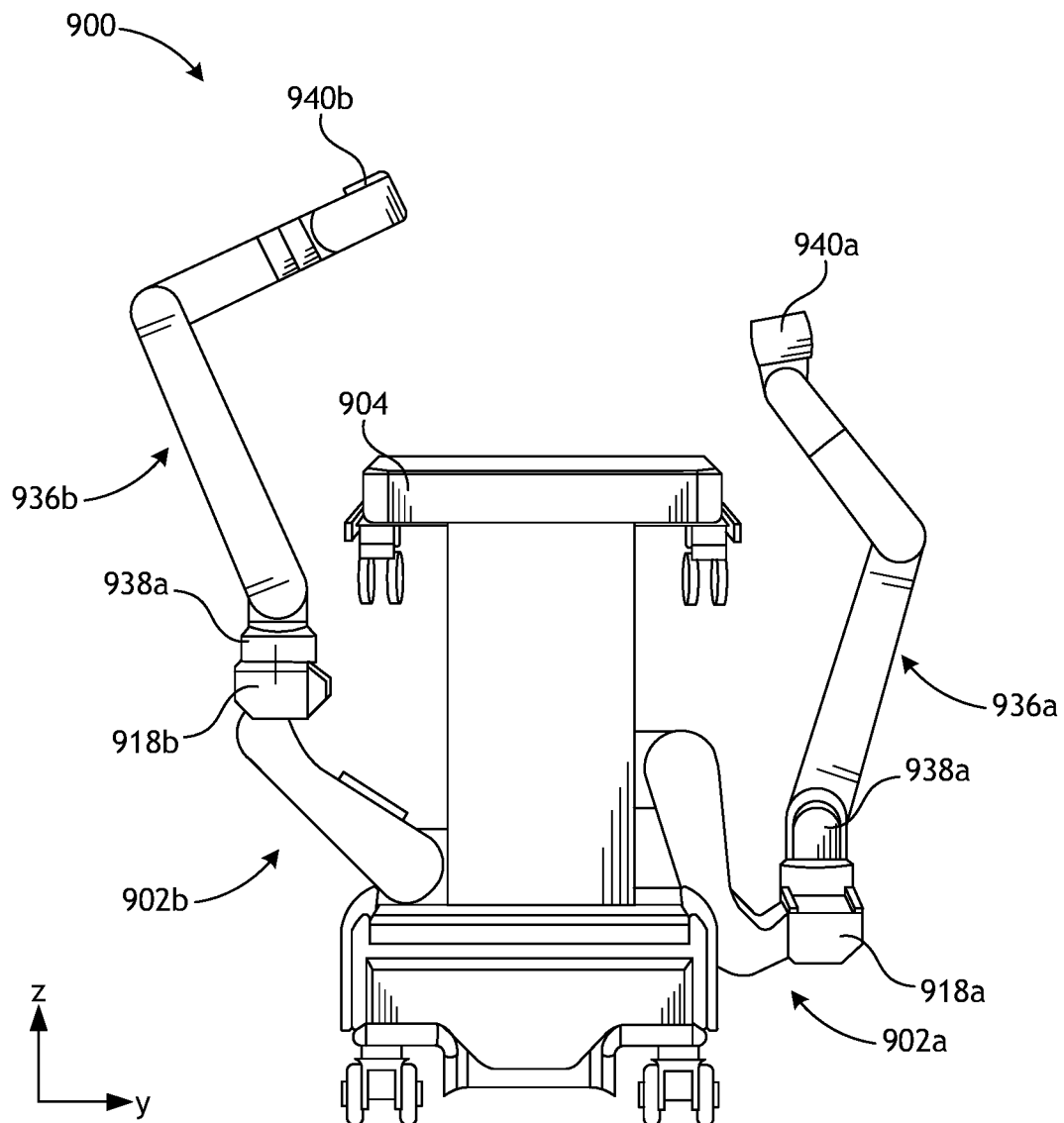
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electromechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
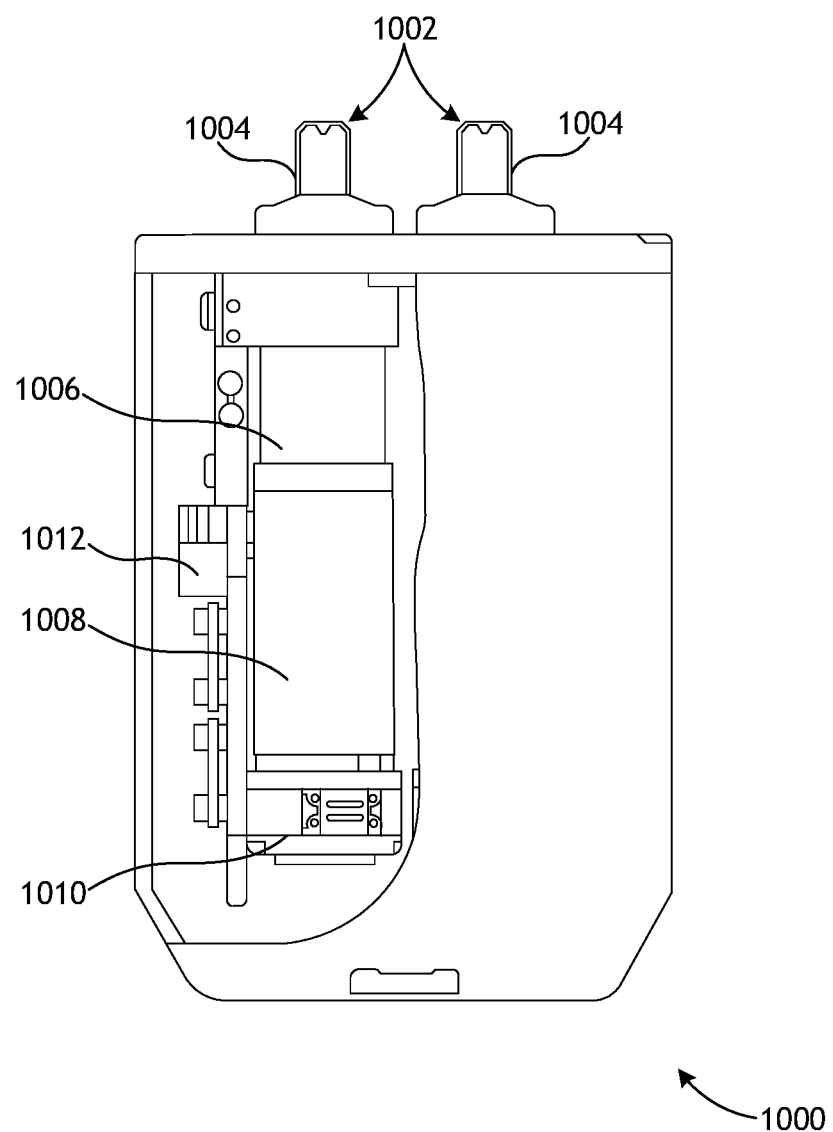
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
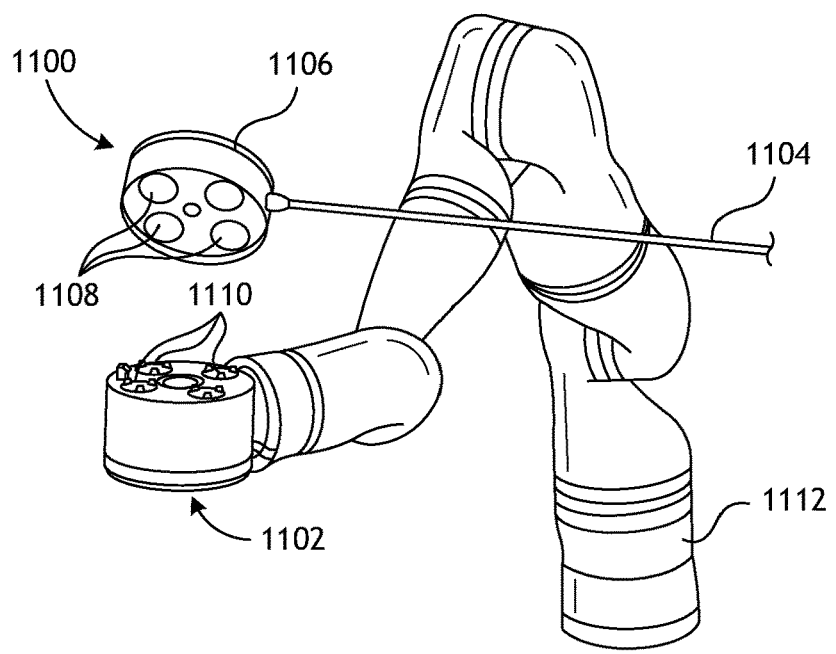
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
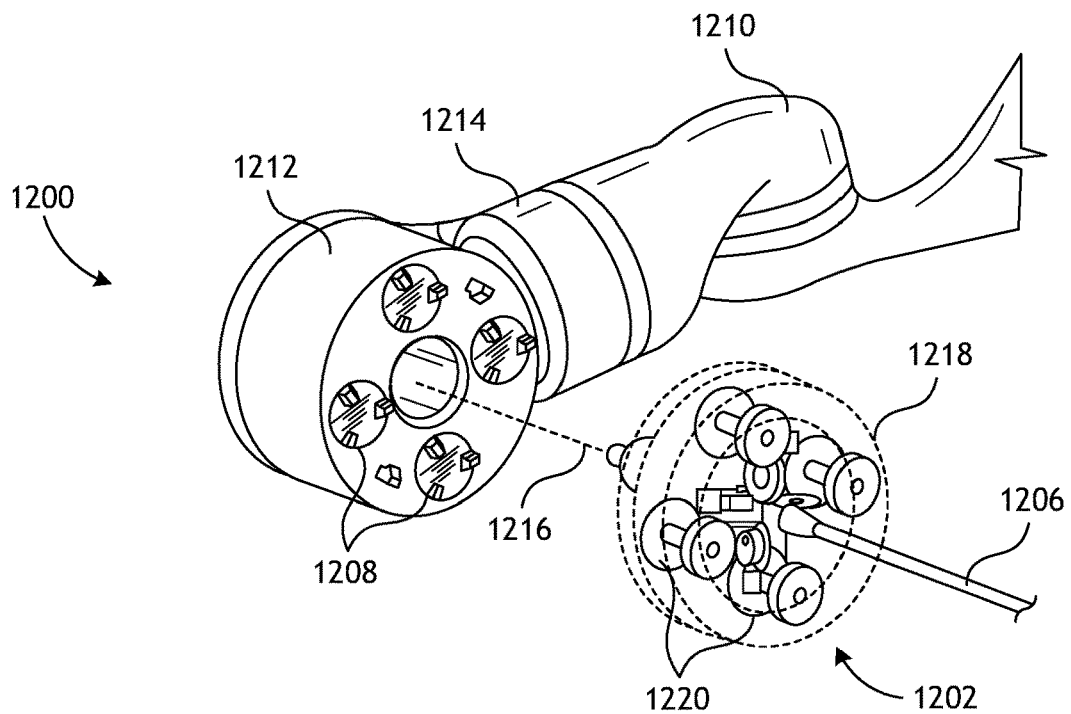
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
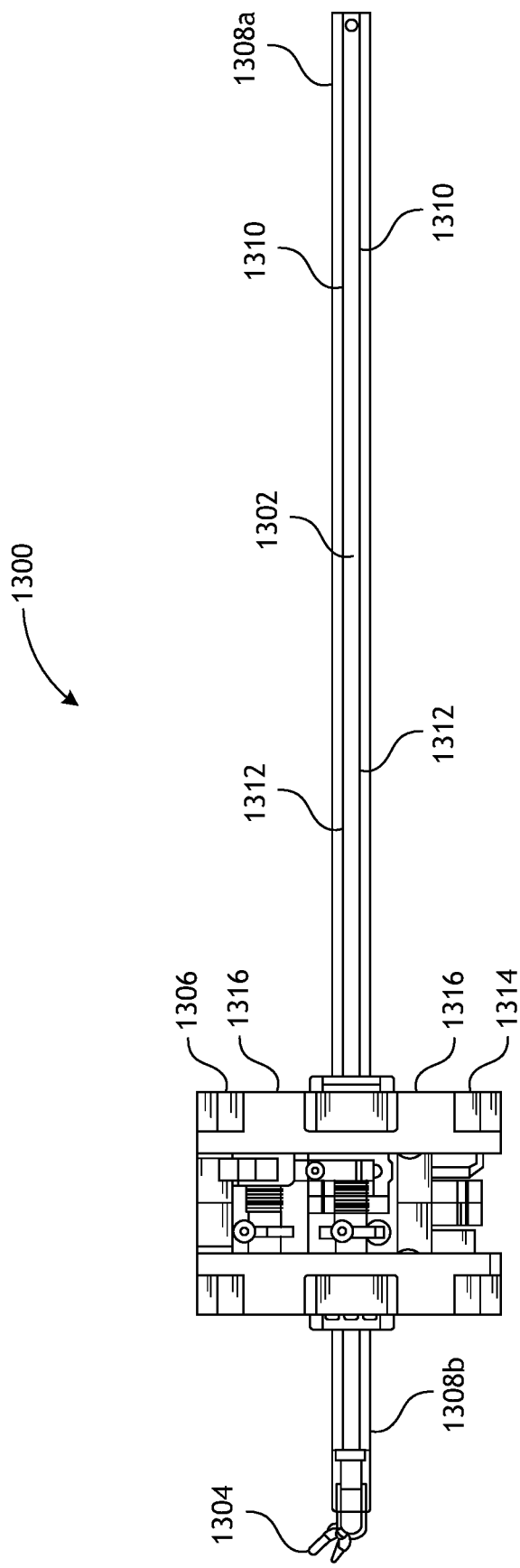
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
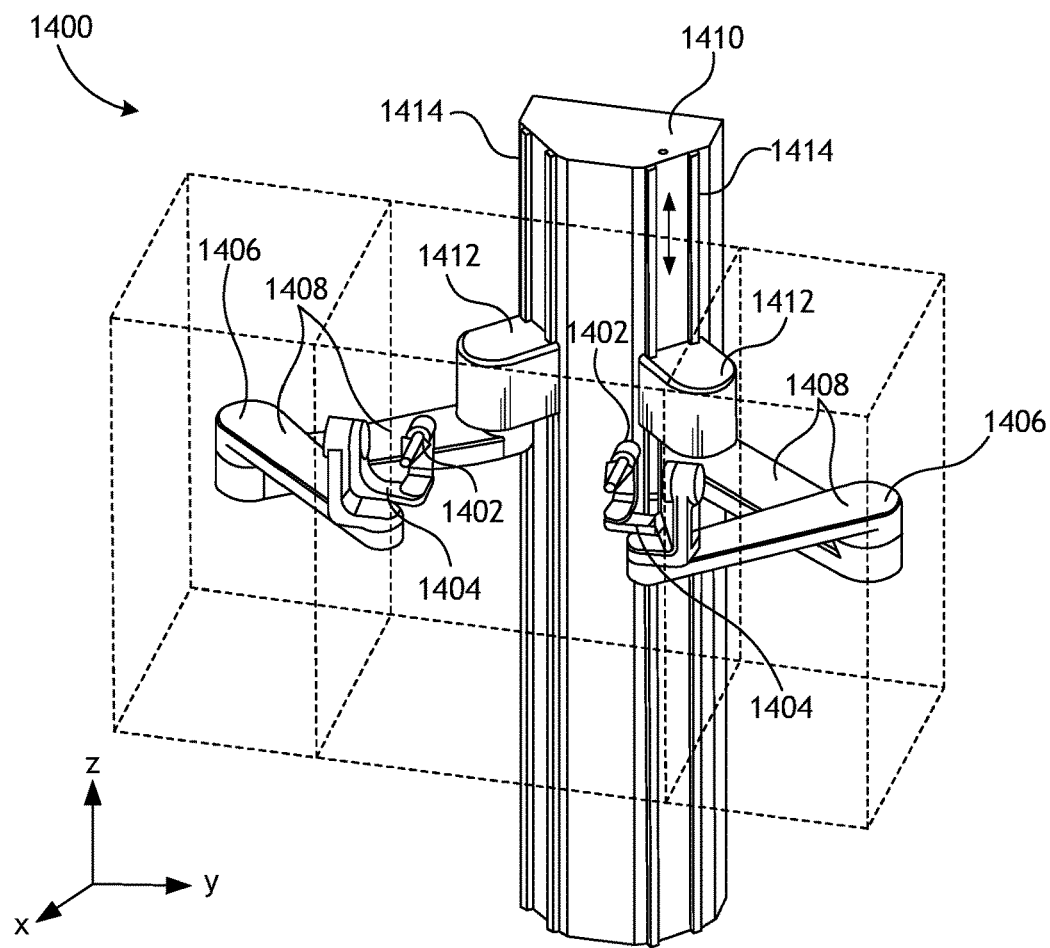
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
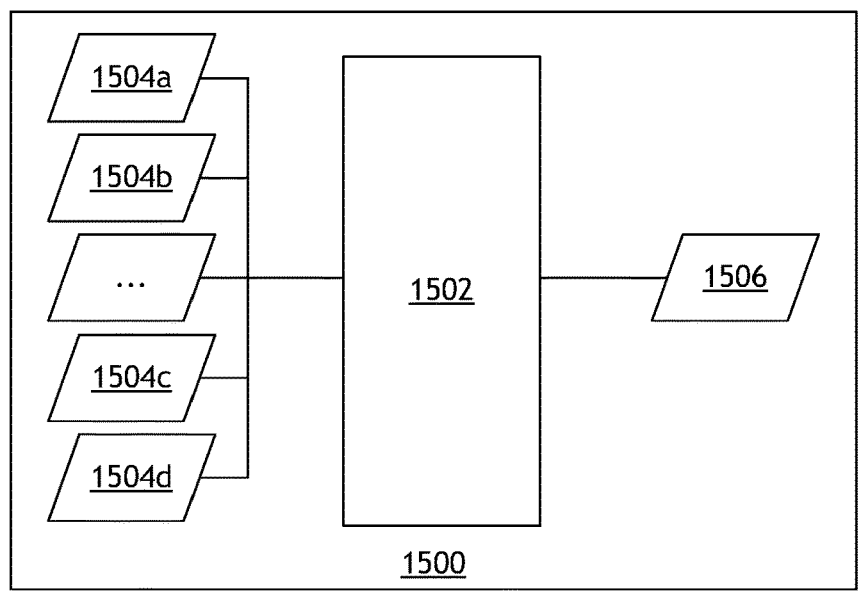
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description

Figure 16:
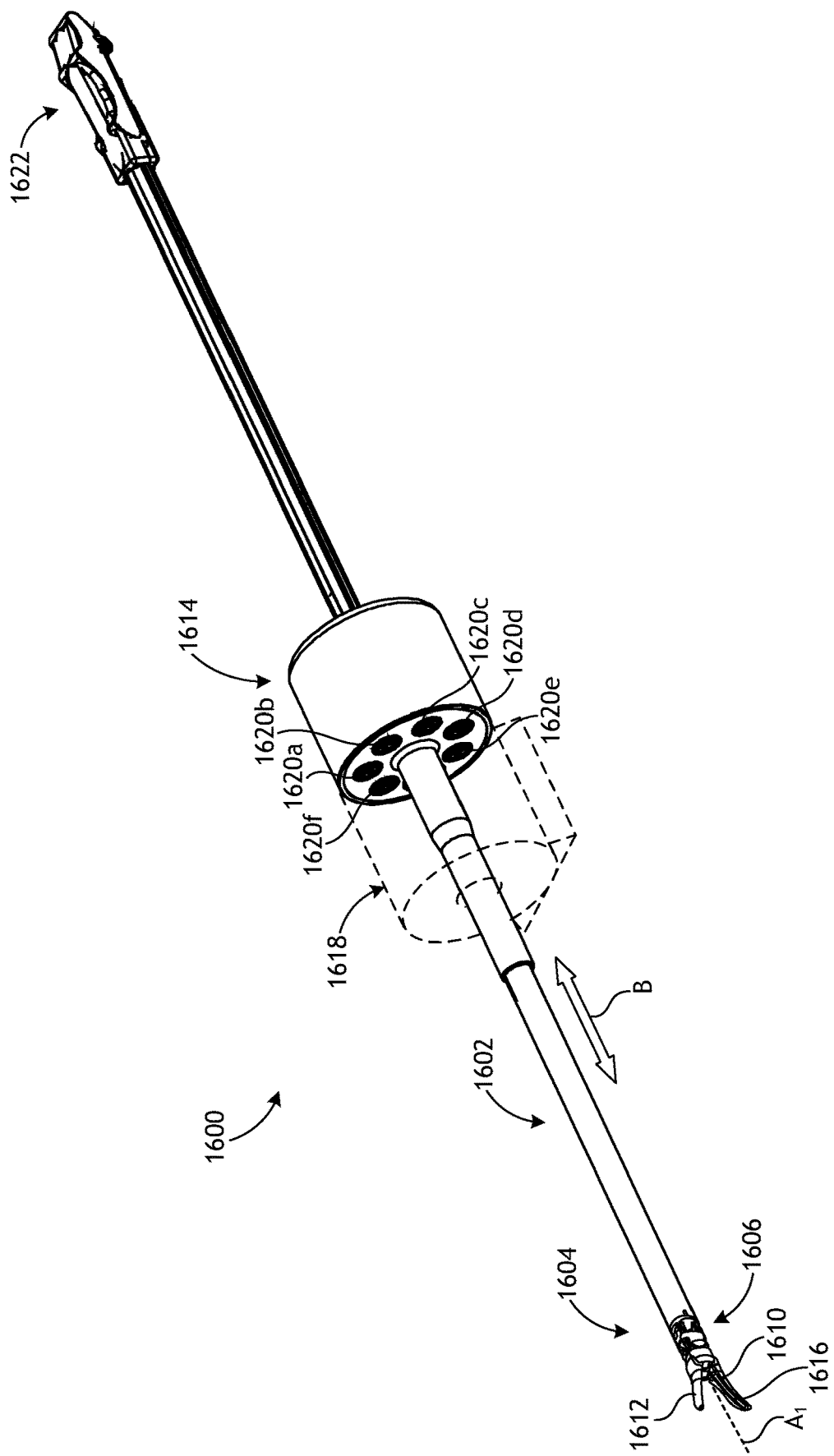
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a vessel sealer capable of cutting and cauterizing/sealing tissue or vessels. The end effector 1604 includes opposing jaws 1610, 1612 configured to move (articulate) between open and closed positions. Alternatively, the end effector 1604 may comprise other types of instruments with opposing jaws such as, but not limited to, a surgical stapler, tissue graspers, surgical scissors, clip appliers, needle drivers, a babcock including a pair of opposed grasping jaws, bipolar jaws (e.g., bipolar Maryland grasper, forceps, a fenestrated grasper, etc.), etc.

One or both of the jaws 1610, 1612 may be configured to pivot to actuate the end effector 1604 between open and closed positions. In the illustrated example, both jaws 1610, 1612 simultaneously move to pivot the jaws 1610, 1612 between an open, unclamped position and a closed, clamped position and are thus referred to as "bifurcating" jaws. In other embodiments, however, only one of the jaws 1610, 1612 may be rotatable (pivotable) relative to the opposing jaw to actuate the end effector 1604 between the open and closed positions.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis A1 of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis A1 of the shaft 1602, such that the end effector 1604 is at a substantially zero angle relative to the shaft 1602. In the articulated position, the longitudinal axis of the end effector 1604 would be angularly offset from the longitudinal axis A1 such that the end effector 1604 would be oriented at a non-zero angle relative to the shaft 1602.

Still referring to FIG. 16, the surgical tool 1600 may include a drive housing or "handle" 1614, and the shaft 1602 extends longitudinally through the handle 1614. The handle 1614 houses an actuation system designed to move the shaft 1602 relative to (through) the handle 1614, and further designed to facilitate articulation of the wrist 1606 and actuation (operation) of the end effector 1604 (e.g., clamping, firing, rotation, articulation, energy delivery, etc.). More specifically, the systems and mechanisms housed within the handle 1614 are actuatable to move (translate) a plurality of drive members that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

Selective actuation of one or more of the drive members, for example, may cause the shaft 1602 to translate relative to the handle 1614, as indicated by the arrows B, and thereby advance or retract the end effector 1602. Selective actuation of one or more other drive members may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" 1616 defined in the first jaw 1610. As it moves distally within the guide track 1616, the knife transects any tissue grasped between the opposing jaws 1610, 1612. In at least one embodiment, actuating the end effector 1604 may further entail triggering energy delivery (e.g., RF energy) to cauterize and/or seal tissue or vessels grasped between the jaws 1610, 1612.

The handle 1614 provides or otherwise includes various coupling features that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the systems and mechanisms housed within the handle 1614 and thereby operate the surgical tool 1600. In the illustrated embodiment, the handle 1614 includes a first drive input 1620*a*, a second drive input 1620*b*, a third drive input 1620*c*, a fourth drive input 1620*d*, a fifth drive input 1620*e*, and a sixth drive input 1620*f*. While six drive inputs 1620*a-f* are depicted, more or less than six may be included in the handle 1614 depending on the application, and without departing from the scope of the disclosure. Each drive input 1620*a-f* may be matable with a corresponding drive output (not shown) of the instrument driver 1618 such that movement (rotation) of a given drive output correspondingly moves (rotates) the associated drive input 1620*a-f* and thereby causes various operations of the surgical tool 1600.

In some embodiments, actuation of the first drive input 1620*a* may cause the knife to fire at the end effector 1604, thus advancing or retracting the knife, depending on the rotational direction of the first drive input 1620*a*. Actuation of the third drive input 1620*c* may cause the shaft 1602 to move (translate) relative to the handle 1614 along the longitudinal axis A1, depending on the rotational direction of the third drive input 1620*c*. In some embodiments, actuation of the second drive input 1620*b* may shift operation or activation within the handle 1614 between the first and third drive inputs 1620*a,c*. Consequently, actuation of the second drive input 1620*b* may dictate whether the knife is fired or whether the shaft 1602 is moved (translated). Actuation of the fourth drive input 1620*d* may lock and unlock z-axis translation of the shaft 1602, and actuation of the fifth drive input 1620*e* may cause articulation of the end effector 1604 at the wrist 1606. Lastly, actuation of the sixth drive input 1620*f* may cause the jaws 1610, 1612 to open or close, depending on the rotational direction of the sixth drive input 1620*f*. In some embodiments, actuation of the sixth drive input 1620*f* may operate a toggle mechanism 1622 arranged at the proximal end of the shaft 1602, and actuation of the toggle mechanism 1622 may cause the jaws 1610, 1612 to open and close. Those skilled in the art, however, will readily appreciate that the handle 1614 may be alternatively designed such that the drive inputs 1620*a-f* carry out other functions, without departing from the scope of the disclosure. Indeed, the operations described above for the drive inputs 1620*a-f* are merely provided as examples, and alternative configurations or operations may instead be provided.

Figure 17:
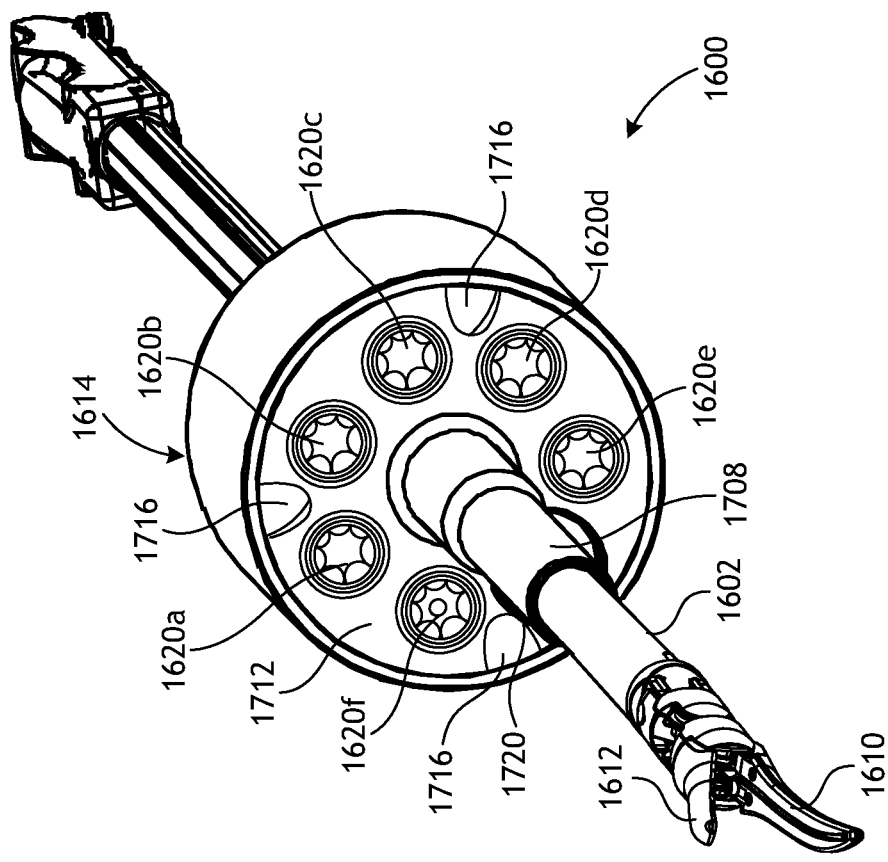
FIG. 17 depicts separated isometric end views of the instrument driver and the surgical tool of FIG. 16.
Figure 17:
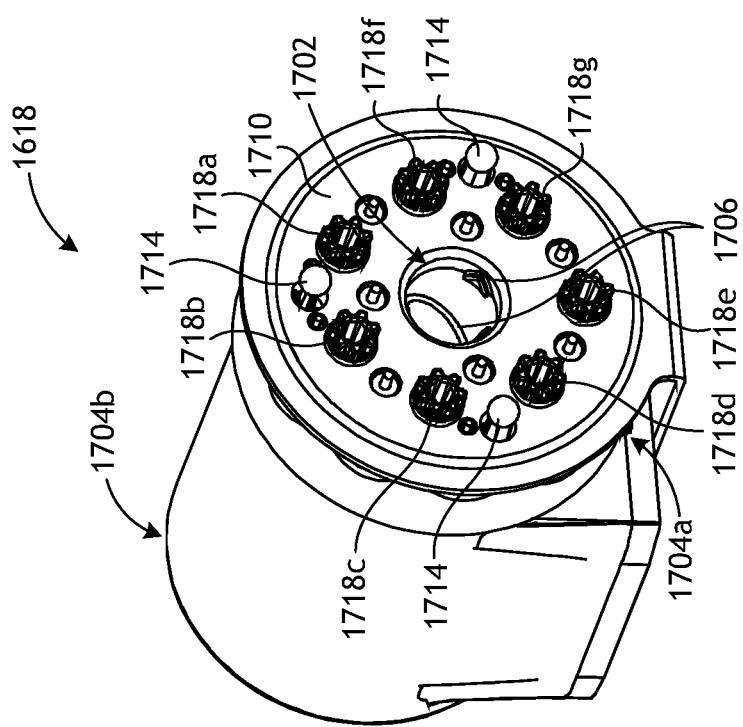

FIG. 17 depicts separated isometric end views of the instrument driver 1618 and the surgical tool 1600 of FIG. 16. With the jaws 1610, 1612 closed, the shaft 1602 and the end effector 1604 can penetrate the instrument driver 1618 by extending through a central aperture 1702 defined longitudinally through the instrument driver 1618 between first and second ends 1704*a,b*. In some embodiments, to align the surgical tool 1600 with the instrument driver 1618 in a proper angular orientation, one or more alignment guides 1706 may be provided or otherwise defined within the central aperture 1702 and configured to engage one or more corresponding alignment features (not shown) provided on the surgical tool 1600. The alignment feature(s) may comprise, for example, a protrusion or projection (not shown) defined on or otherwise provided by an alignment nozzle 1708 extending distally from the handle 1614. In one or more embodiments, the alignment guide(s) 1706 may comprise a curved or arcuate shoulder or lip configured to receive and guide the alignment feature as the alignment nozzle 1708 enters the central aperture 1702. As a result, the surgical tool 1600 is oriented to a proper angular alignment with the instrument driver 1618 as the alignment nozzle 1708 is advanced distally through the central aperture 1702. In other embodiments, the alignment nozzle 1708 may be omitted and the alignment feature 1712 may alternatively be provided on the shaft 1602, without departing from the scope of the disclosure.

A drive interface 1710 is provided at the first end 1704*a* of the instrument driver 1618 and is matable with a driven interface 1712 provided on the distal end of the handle 1614. The drive and driven interfaces 1710, 1712 may be configured to mechanically, magnetically, and/or electrically couple the handle 1614 to the instrument driver 1618. To accomplish this, in some embodiments, the drive and driven interfaces 1710, 1712 may provide one or more matable locating features configured to secure the handle 1614 to the instrument driver 1618. In the illustrated embodiment, for example, the drive interface 1710 provides one or more interlocking features 1714 (three shown) configured to locate and mate with one or more complementary-shaped pockets 1716 (two shown, one occluded) provided on the driven interface 1712. In some embodiments, the features 1714 may be configured to align and mate with the pockets 1716 via an interference or snap fit engagement, for example.

The instrument driver 1618 also includes one or more drive outputs that extend through the drive interface 1710 to mate with corresponding drive inputs 1620*a-f* provided at the distal end of the handle 1614. More specifically, the instrument driver 1618 includes a first drive output 1718*a* matable with the first drive input 1620*a*, a second drive output 1718*b* matable with the second drive input 1620*b*, a third drive output 1718*b* matable with the third drive input 1620*c*, a fourth drive output 1718*d* matable with the fourth drive input 1620*d*, a fifth drive output 1718*e* matable with the fifth drive input 1620*e*, and a sixth drive output 1718*f* matable with the sixth drive input 1620*f*. In some embodiments, as illustrated, the drive outputs 1718*a-f* may define splines or other mechanical features designed to mate with corresponding splined receptacles of the drive inputs 1620a-f. Once properly mated, the drive inputs 1620a-f will share axes of rotation with the corresponding drive outputs 1718a-f to allow the transfer of rotational torque from the drive outputs 1718a-f to the corresponding drive inputs 1620a-f. In some embodiments, each drive output 1718a-f may be spring loaded and otherwise biased to spring outwards away from the drive interface 1710. Each drive output 1718a-f may be capable of partially or fully retracting into the drive interface 1710.

In some embodiments, the instrument driver 1618 may include additional drive outputs, depicted in FIG. 17 as a seventh drive output 1718g. The seventh drive output 1718g may be configured to mate with additional drive inputs (not shown) of the handle 1614 to help undertake one or more additional functions of the surgical tool 1600. In the illustrated embodiment, however, the handle 1614 does not include additional drive inputs matable with the seventh drive output 1718g. Instead, the driven interface 1712 defines a corresponding recess 1720 (partially occluded) configured to receive the seventh drive output 1718g. In other applications, however, a seventh drive input (not shown) could be included in the handle 1614 to mate with the seventh drive output 1718g, or the surgical tool 1600 might be replaced with another surgical tool having a seventh drive input, which would be driven by the seventh drive output 1718g.

While not shown, in some embodiments, an instrument sterile adapter (ISA) may be placed at the interface between the instrument driver 1618 and the handle 1614. In such applications, the interlocking features 1714 may operate as alignment features and possible latches for the ISA to be placed, stabilized, and secured. Stability of the ISA may be accomplished by a nose cone feature provided by the ISA and extending into the central aperture 1702 of the instrument driver 1618. Latching can occur either with the interlocking features 1714 or at other locations at the interface. In some cases, the ISA will provide the means to help align and facilitate the latching of the surgical tool 1600 to the ISA and simultaneously to the instrument driver 1618.

Figure 18:
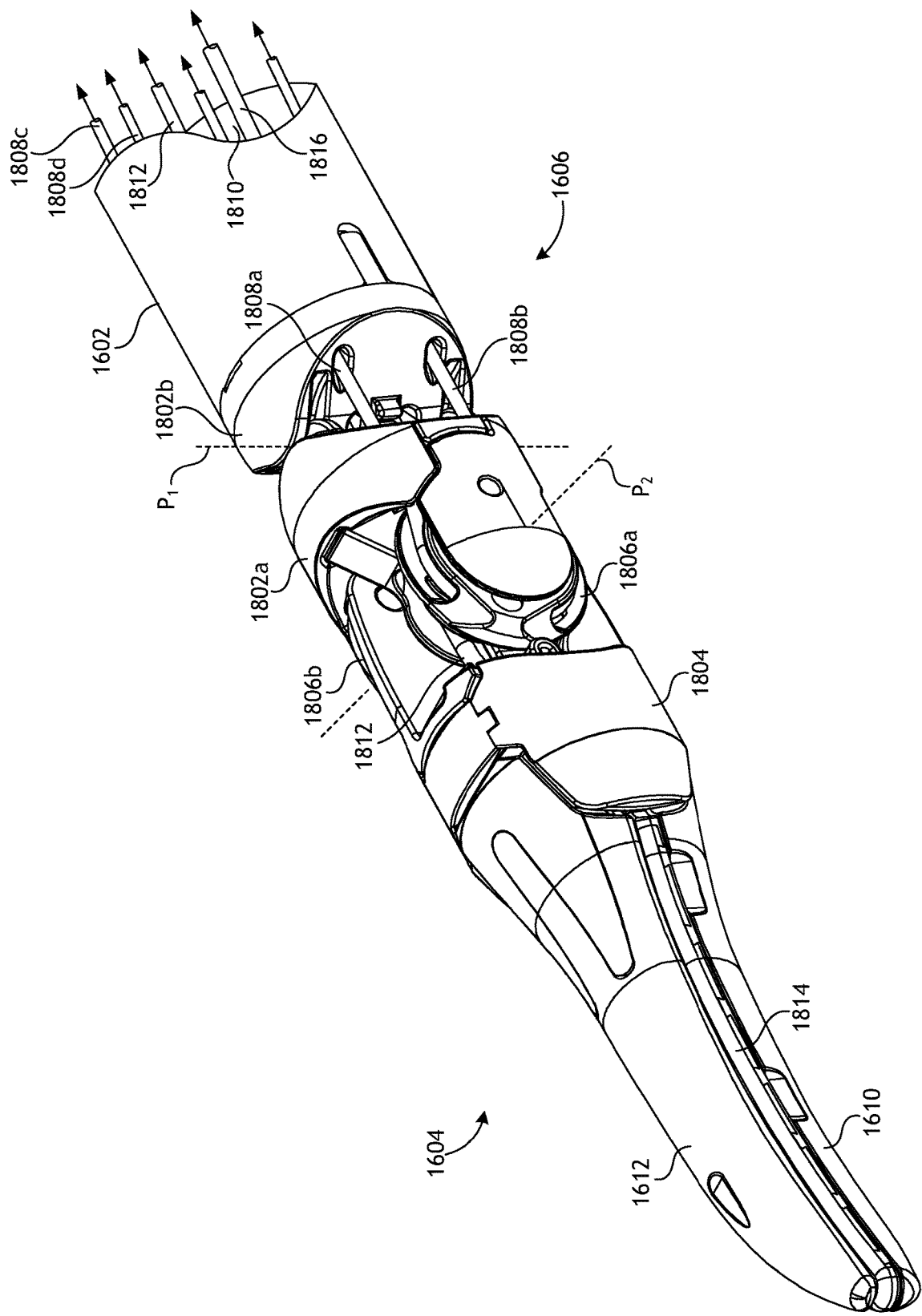
FIG. 18 is an enlarged isometric view of the distal end of the surgical tool of FIGS. 16 and 17, according to one or more embodiments.

FIG. 18 is an enlarged isometric view of the distal end of the surgical tool 1600 of FIGS. 16 and 17. As illustrated, the wrist 1606 interposes the shaft 1602 and the end effector 1604 and thereby operatively couples the end effector 1604 to the shaft 1602. In some embodiments, however, a shaft adapter may be directly coupled to the wrist 1606 and otherwise interpose the shaft 1602 and the wrist 1606. Accordingly, the wrist 1606 may be operatively coupled to the shaft 1602 either through a direct coupling engagement where the wrist 1606 is directly coupled to the distal end of the shaft 1602, or an indirect coupling engagement where a shaft adapter interposes the wrist 1606 and the distal end of the shaft 1602. As used herein, the term "operatively couple" refers to a direct or indirect coupling engagement between two components.

To operatively couple the end effector 1604 to the shaft 1602, the wrist 1606 includes a first or "distal" clevis 1802a and a second or "proximal" clevis 1802b. The clevises 1802a,b are alternatively referred to as "articulation joints" of the wrist 1606 and extend from the shaft 1602, or alternatively a shaft adapter. The clevises 1802a,b are operatively coupled to facilitate articulation of the wrist 1606 relative to the shaft 1602. As illustrated, the wrist 1606 also includes a linkage 1804 arranged distal to the distal clevis 1802a and operatively mounted to the jaws 1610, 1612.

As illustrated, the proximal end of the distal clevis 1802a may be rotatably mounted or pivotably coupled to the proximal clevis 1802b at a first pivot axis P1 of the wrist 1602. In some embodiments, an axle may extend through the first pivot axis P1 and the distal and proximal clevises 1802a,b may be rotatably coupled via the axle. In other embodiments, however, such as is depicted in FIG. 18, the distal and proximal clevises 1802a,b may be engaged in rolling contact, such as via an intermeshed gear relationship (not shown) that allows the clevises 1802a,b to rotate relative to each other similar to a rolling joint. Accordingly, the first pivot axis P1 will be referred to herein as the rolling joint P1.

First and second pulleys 1806a and 1806b may be rotatably mounted to the distal end of the distal clevis 1802a at a second pivot axis P2 of the wrist 1602. The linkage 1804 may be arranged distal to the second pivot axis P2 and operatively mounted to the jaws 1610, 1612. The rolling joint P1 is substantially perpendicular (orthogonal) to the longitudinal axis A1 of the shaft 1602, and the second pivot axis P2 is substantially perpendicular (orthogonal) to both the longitudinal axis A1 and the rolling joint P1. Movement of the end effector 1604 about the rolling joint P1 provides "yaw" articulation of the wrist 1606, and movement about the second pivot axis P2 provides "pitch" articulation of the wrist 1606.

A plurality of drive members, shown as drive members 1808a, 1808b, 1808c, and 1808d, extend longitudinally within a lumen 1810 defined by the shaft 1602 (or a shaft adaptor) and extend at least partially through the wrist 1606. The drive members 1808a-d may form part of the actuation systems housed within the handle 1614 (FIGS. 16 and 17), and may comprise cables, bands, lines, cords, wires, woven wires, ropes, strings, twisted strings, elongate members, belts, shafts, flexible shafts, drive rods, or any combination thereof. The drive members 1808a-d can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof. While four drive members 1808a-d are depicted in FIG. 18, more or less than four may be employed, without departing from the scope of the disclosure.

The drive members 1808a-d extend proximally from the end effector 1604 and the wrist 1606 toward the handle 1614 (FIGS. 16 and 17) where they are operatively coupled to various actuation mechanisms or devices that facilitate longitudinal movement (translation) of the drive members 1808a-d within the lumen 1810. Selective actuation of the drive members 1808a-d applies tension (i.e., pull force) to the given drive member 1808a-d in the proximal direction, which urges the given drive member 1808a-d to translate longitudinally within the lumen 1810.

In the illustrated embodiment, the drive members 1808a-d each extend longitudinally through the proximal clevis 1802b. The distal end of each drive member 1808a-d terminates at the first or second pulleys 1806a,b, thus operatively coupling each drive member 1808a-d to the end effector 1604. In some embodiments, the distal ends of the first and second drive members 1808a,b may be coupled to each other and terminate at the first pulley 1806a, and the distal ends of the third and fourth drive members 1808c,d may be coupled to each other and terminate at the second pulley 1806b. In at least one embodiment, the distal ends of the first and second drive members 1808a,b and the distal ends of the third and fourth drive members 1808c,d may each be coupled together at corresponding ball crimps (not shown) mounted to the first and second pulley 1806a,b, respectively.

In at least one embodiment, the drive members 1808a-d may operate "antagonistically". More specifically, when the first drive member 1808a is actuated (moved), the second drive member 1808b naturally follows as coupled to the first drive member 1808a, and when the third drive member 1808c is actuated, the fourth drive member 1808d naturally follows as coupled to the third drive member 1808c, and vice versa. Antagonistic operation of the drive members 1808a-d can open or close the jaws 1610, 1612 and can further cause the end effector 1604 to articulate at the wrist 1606. More specifically, selective actuation of the drive members 1808a-d in known configurations or coordination can cause the end effector 1604 to articulate about one or both of the pivot axes P1, P2, thus facilitating articulation of the end effector 1604 in both pitch and yaw directions. Moreover, selective actuation of the drive members 1808a-d in other known configurations or coordination will cause the jaws 1610, 1612 to open or close. Antagonistic operation of the drive members 1808a-d advantageously reduces the number of cables required to provide full wrist 1606 motion, and also helps eliminate slack in the drive members 1808a-d, which results in more precise motion of the end effector 1604.

In the illustrated embodiment, the end effector 1604 is able to articulate (move) in pitch about the second or "pitch" pivot axis P2, which is located near the distal end of the wrist 1606. Thus, the jaws 1610, 1612 open and close in the direction of pitch. In other embodiments, however, the wrist 1606 may alternatively be configured such that the second pivot axis P2 facilitates yaw articulation of the jaws 1610, 1612, without departing from the scope of the disclosure.

In some embodiments, an electrical conductor 1812 may also extend longitudinally within the lumen 1810, through the wrist 1606, and terminate at an electrode 1814 to supply electrical energy to the end effector 1604. In some embodiments, the electrical conductor 1812 may comprise a wire, but may alternatively comprise a rigid or semi-rigid shaft, rod, or strip (ribbon) made of a conductive material. The electrical conductor 1812 may be entirely or partially covered with an insulative covering (overmold) made of a non-conductive material. Using the electrical conductor 1812 and the electrode 1814, the end effector 1604 may be configured for monopolar or bipolar RF operation.

In the illustrated embodiment, the end effector 1604 comprises a combination tissue grasper and vessel sealer that includes a knife (not shown), alternately referred to as a "cutting element" or "blade." The knife is aligned with and configured to traverse the guide track 1616 (FIG. 16) defined longitudinally in one or both of the upper and lower jaws 1610, 1612. The knife may be operatively coupled to the distal end of a drive rod 1816 that extends longitudinally within the lumen 1810 and passes through the wrist 1606. Longitudinal movement (translation) of the drive rod 1816 correspondingly moves the knife within the guide track(s) 1616. Similar to the drive members 1808a-d, the drive rod 1816 may form part of the actuation systems housed within the handle 1614 (FIGS. 16 and 17). Selective actuation of a corresponding drive input will cause the drive rod 1816 to move distally or proximally within the lumen 1810, and correspondingly move the knife 1816 in the same longitudinal direction.

Figure 19A:
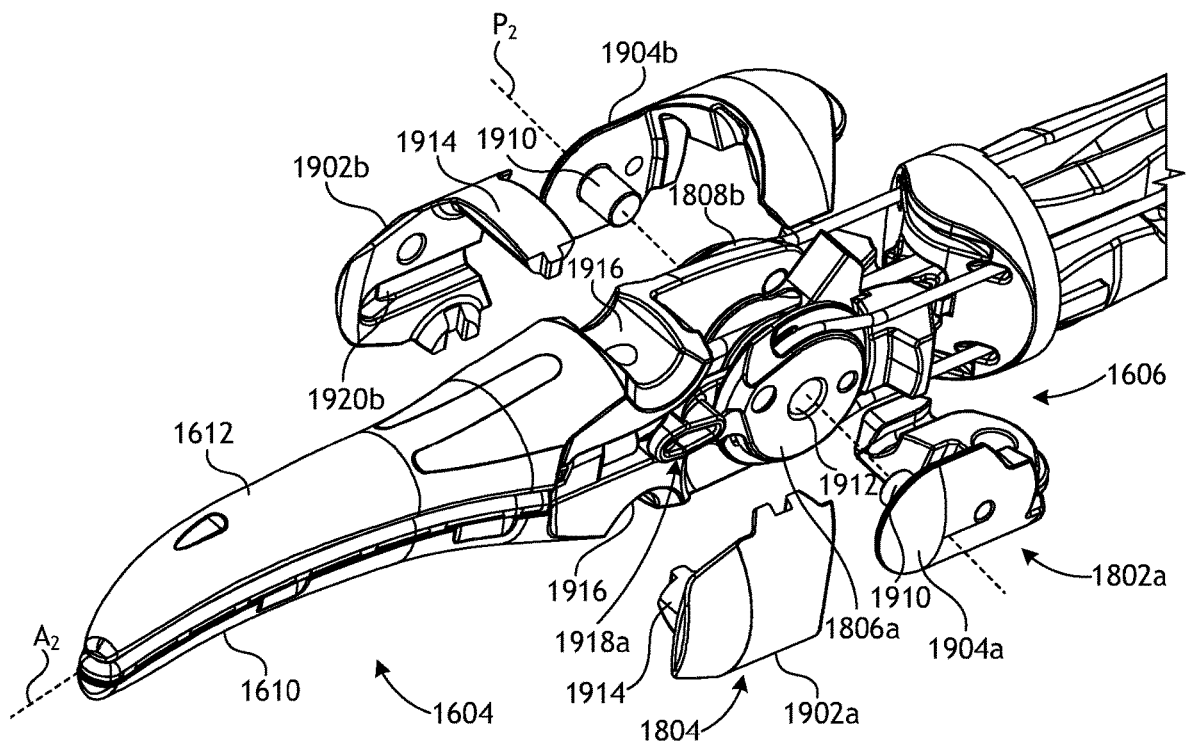
FIGS. 19A and 19B are isometric, partially exploded views of the end effector of FIG. 18 from right and left vantage points, respectively, according to one or more embodiments.
Figure 19B:
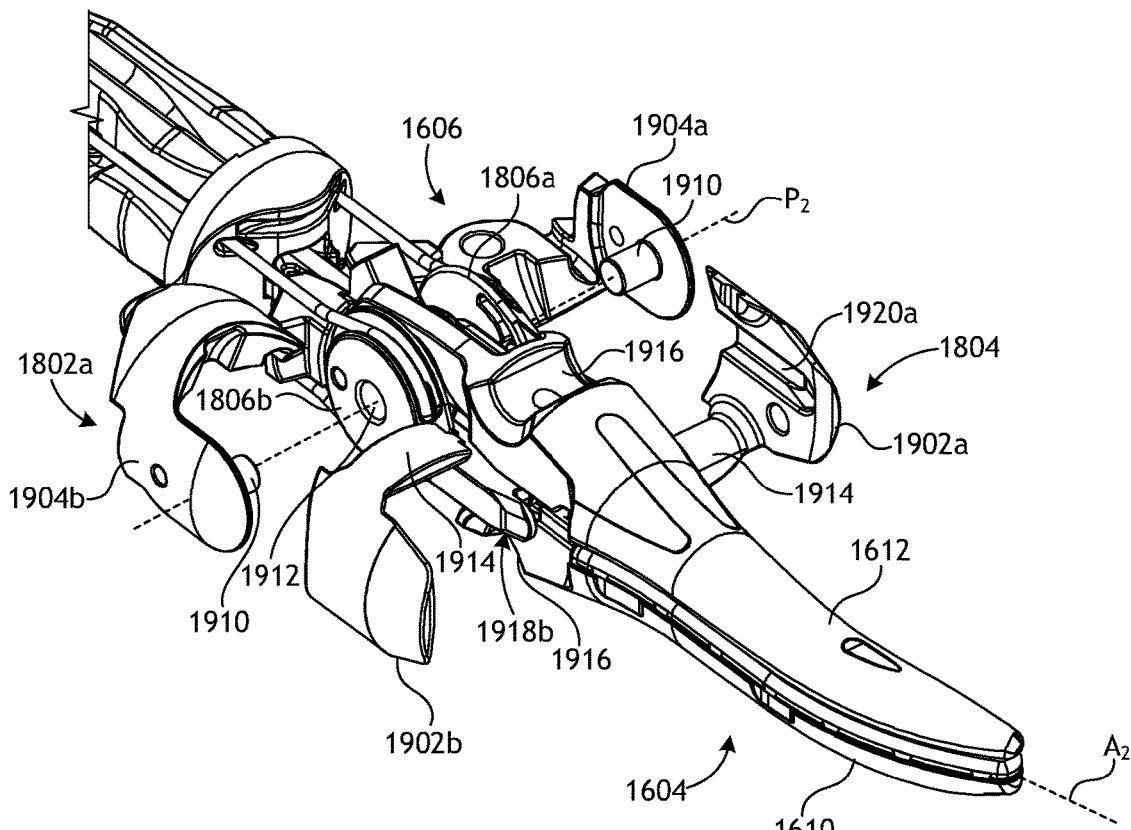

FIGS. 19A and 19B are isometric, partially exploded views of the end effector 1604 of FIG. 18, as taken from right and left vantage points, respectively. FIGS. 19A-19B depict the distal clevis 1802a and the linkage 1804 exploded laterally from the remaining portions of the end effector 1604 and the wrist 1606, thus exposing the distal ends of the drive members 1808a-d terminating at the pulleys 1806a,b.

In some embodiments, as illustrated, one or both of the distal clevis 1802a and the linkage 1804 may comprise two or more component parts that are joined to help form the wrist 1606 and rotatably secure the jaws 1610, 1612 to the wrist 1606. In the illustrated embodiment, for example, the linkage 1804 comprises opposing first and second linkage portions 1902a,b, and the distal clevis 1802a comprises opposing first and second distal clevis portions 1904a,b. In building the wrist 1606, joining the linkage portions 1902a,b and joining the distal clevis portions 1904a,b may help rotatably secure the jaws 1610, 1612 to the wrist 1606 and may further secure the pulleys 1806a,b and other component parts within the wrist 1606. The linkage portions 1902a,b and the distal clevis portions 1904a,b may be joined, respectively, by welding, soldering, brazing, an adhesive, an interference fit, or by using one or more mechanical fasteners, such as pins, rivets, screws, bolts, or any combination of the foregoing. In other embodiments, however, it is contemplated herein that one or both of the distal clevis 1802a and the linkage 1804 may alternatively comprise a monolithic, one-piece structure, without departing from the scope of the disclosure.

As indicated above, the first and second pulleys 1806a,b may be rotatably mounted to the distal end of the distal clevis 1802a at the second pivot axis P2 of the wrist 1602. As illustrated, the distal clevis 1802a may provide or otherwise define opposing pins 1910 and the pulleys 1806a,b may each define an aperture 1912 sized to receive or mate with a corresponding one of the pins 1910. In alternative embodiments, however, the pins 1910 may be provided by the pulleys 1806a,b, and the apertures 1912 may be provided by the distal clevis 1802a, without departing from the scope of the disclosure. Moreover, in some embodiments, the apertures 1912 need not be through-holes, as depicted, but could alternatively comprise recesses or pockets defined in the pulleys 1806a,b (or the distal clevis 1802a) and sized and otherwise configured to receive the pins 1910.

As also indicated above, the linkage 1804 may be mounted or otherwise operatively coupled to the jaws 1610, 1612. As illustrated, the linkage 1804 may provide or define one or more lateral arms 1914 and the jaws 1610, 1612 may define a corresponding one or more grooves 1916 configured to receive the lateral arms 1914 and provide corresponding inner jaw pivot surfaces for the jaws 1610, 1612. In the illustrated embodiment, one lateral arm 1914 is received within the groove 1916 defined by the first jaw 1610, and the other lateral arm 1914 is received within the groove 1916 defined by the second jaw 1612. Receiving the lateral arms 1914 in the grooves 1916 creates a jaw pivot point where the jaws 1610, 1612 are able to pivot between the open and closed positions. The lateral arms 1914 interact with the corresponding grooves 1916 and help prevent the jaws 1610, 1612 from separating from each other. In some embodiments, the lateral arms 1914 slidably engage the corresponding grooves 1916 as the jaws 1610, 1612 open and close about the jaw pivot point, thus the grooves 1916 may operate as corresponding cam surfaces. The jaw pivot points created by interaction between the lateral arms 1914 and the grooves 1916 may be substantially parallel to the second pivot axis P2.

The wrist 1606 may further provide a jaw constraint that prevents the jaws 1610, 1612 from rotating out of alignment with each other as the jaws 1610, 1612 open and close, and may also help prevent the jaws 1610, 1612 from inadvertently moving in pitch while opening or closing. In the illustrated embodiment, the jaw constraint includes one or more alignment arms, shown as a first alignment arm 1918a (FIG. 19A) and a second alignment arm 1918b (FIG. 19B). The proximal end of the first alignment arm 1918a may be rotatably coupled (e.g., pinned) to the first pulley 1806a at the second pivot axis P2, and the proximal end of the second alignment arm 1918b may be rotatably coupled (e.g., pinned) to the second pulley 1806b at the second pivot axis P2. In contrast, the distal end of the first alignment arm 1918a may be received within a first slot 1920a (FIG. 19B) defined in the first linkage portion 1902a of the linkage 1804, and the distal end of the second alignment arm 1918b may be received within a second slot 1920b (FIG. 19A) defined in the second linkage portion 1902b of the linkage 1804. The slots 1920a,b extend distally and proximally such that the direction or axis of the slots 1920a,b is generally parallel to a longitudinal axis A2 of the end effector 1604. When the end effector 1604 is in an unarticulated position, the longitudinal axis A2 and the longitudinal axis A1 (FIG. 16) of the shaft 1602 (FIG. 16) are the same and otherwise concentric.

Without the jaw constraint provided by the alignment arms 1918a,b and the corresponding slots 1920a,b, the jaws 1610, 1612 would tend to rotate out of alignment and potentially move in pitch during opening and closing, thus preventing accurate positioning during opening and closing. This jaw condition is sometimes referred to as extreme backlash or slop. While two alignment arms 1918a,b are included in the illustrated embodiments, only one alignment arm 1918a,b may be required for the purposes of the present disclosure.

Figure 20A:
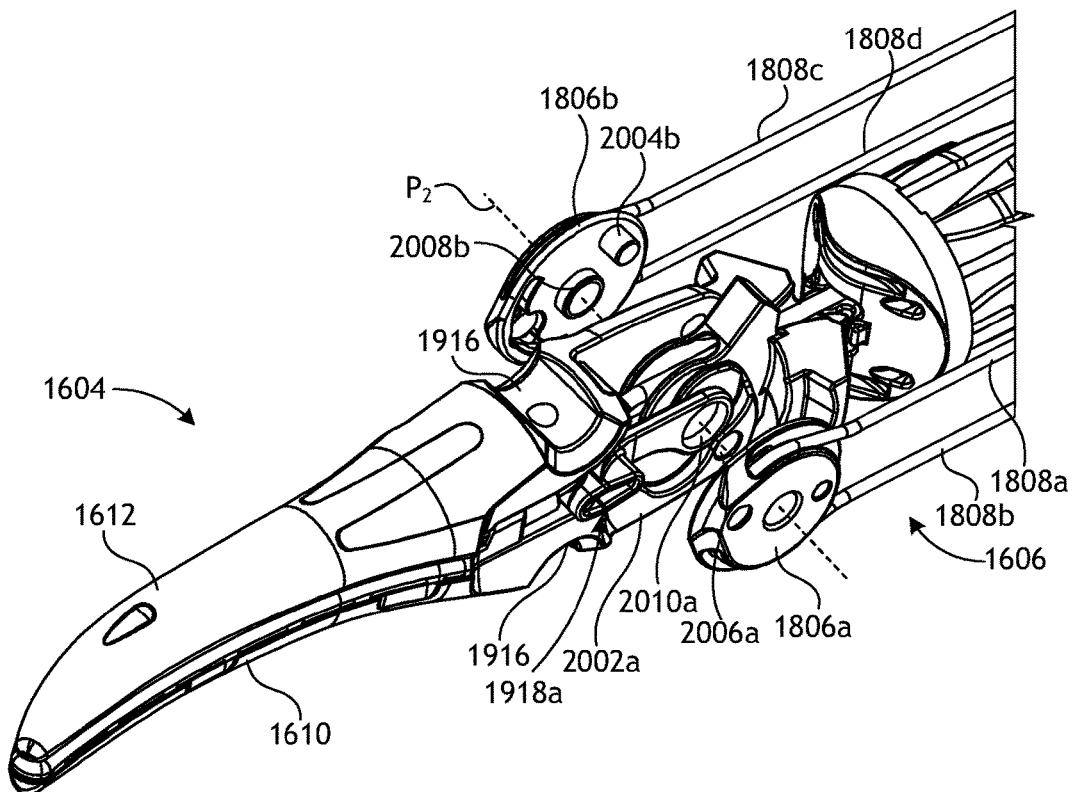
FIGS. 20A and 20B are additional isometric, partially exploded views of the end effector of FIG. 18 from the right and left vantage points.
Figure 20B:
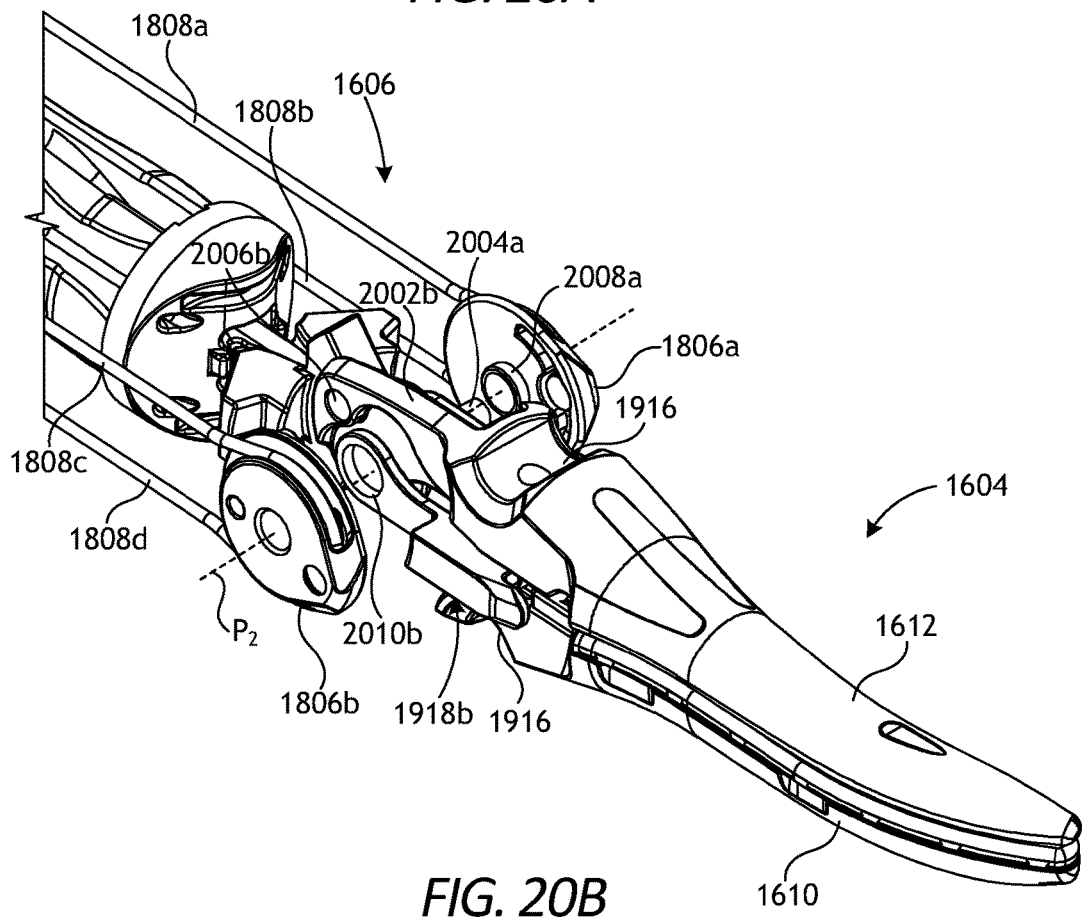

FIGS. 20A and 20B are additional isometric, partially exploded views of the end effector 1604 of FIG. 18 from the right and left vantage points, respectively. In FIGS. 20A-20B, the distal and proximal clevises 1802a,b (FIGS. 19A-19B) are omitted for simplicity, and the first and second pulleys 1806a,b and the drive members 1808a-d are shown exploded laterally from the remaining portions of the end effector 1604 and the wrist 1606.

As illustrated, the first jaw 1610 provides a first jaw extension 2002a (FIG. 20A) and the second jaw 1612 provides a second jaw extension 2002b (FIG. 20B), and each jaw extension 2002a,b extends proximally from the corresponding jaw 1610, 1612. The first jaw extension 2002a may be rotatably coupled (e.g., pinned) to the first pulley 1806a such that movement (rotation) of the first pulley 1806a correspondingly moves the first jaw 1610 to pivot about the jaw pivot point, and the second jaw extension 2002b may be rotatably coupled (e.g. pinned) to the second pulley 1806b such that movement (rotation) of the second pulley 1806b correspondingly moves the second jaw 1612 to pivot about the jaw pivot point.

In the illustrated embodiment, the first pulley 1806a may provide or define a first jaw pin 2004a (FIG. 20B) configured to mate with a first jaw aperture 2006a (FIG. 20A) defined on the first jaw extension 2002a, and the second pulley 1806b may provide or define a second jaw pin 2004b (FIG. 20A) configured to mate with a second jaw aperture 2006b (FIG. 20B) defined on the second jaw extension 2002b. The first and second jaw pins 2004a,b are eccentric to the second pivot axis P2. Consequently, mating the first and second jaw pins 2004a,b with the first and second jaw apertures 2006a,b, respectively, allows the pulleys 1806a,b to rotate about the second pivot axis P2 to pivot the jaws 1610, 1612 about the jaw pivot points and between the open and closed positions, as constrained by the lateral arms 1914 (FIGS. 19A-19B).

In an alternative embodiment, the first and second jaw pins 2004a,b may be provided on the first and second jaw extensions 2002a,b, respectively, and the first and second jaw apertures 2006a,b may be provided on the pulleys 1806a,b, respectively, or any combination thereof. Moreover, the jaw apertures 2006a,b need not be through-holes, as depicted, but could alternatively comprise recesses defined in the jaw extensions 2002a,b (or the pulleys 1806a,b) and sized and otherwise configured to receive the jaw pins 2004a,b.

As mentioned above, the first and second alignment arms 1918a,b may be rotatably coupled (e.g., pinned) to the first and second pulleys 1806a,b, respectively, at the second pivot axis P2. In the illustrated embodiment, for example, the first pulley 1806a may provide or define a first arm pin 2008a (FIG. 20B) configured to mate with a first arm aperture 2010a defined by the first alignment arm 1918a, and the second pulley 1806b may provide or define a second arm pin 2008b (FIG. 20A) configured to mate with a second arm aperture 2010b (FIG. 20B) defined by the second alignment arm 1918b (FIG. 20B). The first and second arm pins 2008a,b are concentric to (with) the second pivot axis P2, thus allowing the pulleys 1806a,b to rotate without directly affecting the position of the alignment arms 1918a,b. However, actuation of the pulleys 1806a,b to open and close the jaws 1610, 1612 may result in the distal ends of the alignment arms 1918a,b sliding (traversing) within the corresponding slots 1920a,b (FIGS. 19A-19B), respectively. This helps maintain the jaws 1610, 1612 moving distally and/or proximally in a straight line during closing and opening (i.e., axial constraint), instead of rotating about the jaw pins 2004a,b.

In an alternative embodiment, the first and second arm pins 2008a,b may be provided on the alignment arms 1918a,b, respectively, and the first and second arm apertures 2010a,b may be provided on the pulleys 1806a,b, respectively, or any combination thereof, without departing from the scope of the disclosure. Moreover, the arm apertures 2010a,b need not be through-holes, as depicted, but could alternatively comprise recesses defined in the alignment arms 1918a,b (or the pulleys 1806a,b) and sized and otherwise configured to receive the arm pins 2008a,b.

As indicated above, selective actuation and antagonistic operation of the drive members 1808a-d can open or close the jaws 1610, 1612. Because the jaws 1610, 1612 are pinned to the pulleys 1806a,b and pivotally constrained at the jaw pivot points by the lateral arms 1914 (FIGS. 19A-19B) at the grooves 1916, as generally described above, selectively actuating the drive members 1808a-d such that the pulleys 1806a,b rotate in opposite angular directions may result in the jaws 1610, 1612 opening or closing. Simultaneously pulling proximally on the first and fourth drive members 1808a,d, for example, while allowing the second and third drive members 1808b,c to pay out slack, will cause the pulleys 1806a,b to rotate in first opposing directions and thereby cause the jaws 1610, 1612 to move (pivot) toward the closed position. In contrast, simultaneously pulling proximally on the second and third drive members 1808b,c while allowing the first and fourth drive members 1808a,d to pay out slack, will cause the pulleys 1806a,b to rotate in second opposing directions opposite the first opposing directions and thereby cause the jaws 1610, 1612 to move (pivot) toward the open position.

As also indicated above, selective actuation and antagonistic operation of the drive members 1808a-d may also cause the end effector 1604 to articulate at the wrist 1606 in both pitch and yaw directions. Again, because the jaws 1610, 1612 are pinned to the pulleys 1806a,b and pivotally constrained at the jaw pivot point by the lateral arms 1914 (FIGS. 19A-19B) at the grooves 1916, selectively actuating the drive members 1808a-d such that the pulleys 1806a,b rotate in the same angular direction may result in the jaws 1610, 1612 pivoting about the second pivot axis P2 and thereby moving the end effector 1604 up or down in pitch. More specifically, simultaneously pulling on the first and third drive members 1808a,c while allowing the second and fourth drive members 1808b,d to pay out slack will cause the pulleys 1808a,b to rotate in a first angular direction and thereby pivot the end effector 1604 about the second pivot axis P2 in upward pitch. In contrast, simultaneously pulling on the second and fourth drive members 1808b,d while allowing the first and third drive members 1808a,c to pay out will cause the pulleys 1808a,b to rotate in a second angular direction opposite the first angular direction and thereby pivot the end effector 1604 about the second pivot axis P2 in downward pitch.

Furthermore, selective actuation of a first connected pair of drive members 1808a-d while relaxing a second pair of connected drive members 1808a-d may cause the end effector 1604 to pivot about the rolling joint P1 (FIG. 18) and thereby move in yaw. More specifically, pulling on the first and second drive members 1808a,b while simultaneously slackening the third and fourth drive members 1808c,d (e.g., allowing the third and fourth drive members 1808c,d to pay out) will pivot the end effector 1604 in yaw in a first direction. In contrast, pulling on the third and fourth drive members 1808c,d while simultaneously slackening the first and second drive members 1808a,b (e.g., allowing the first and second drive members 1808a,b to pay out) will pivot the end effector 1604 in yaw in a second direction opposite the first direction.

Figure 21A:
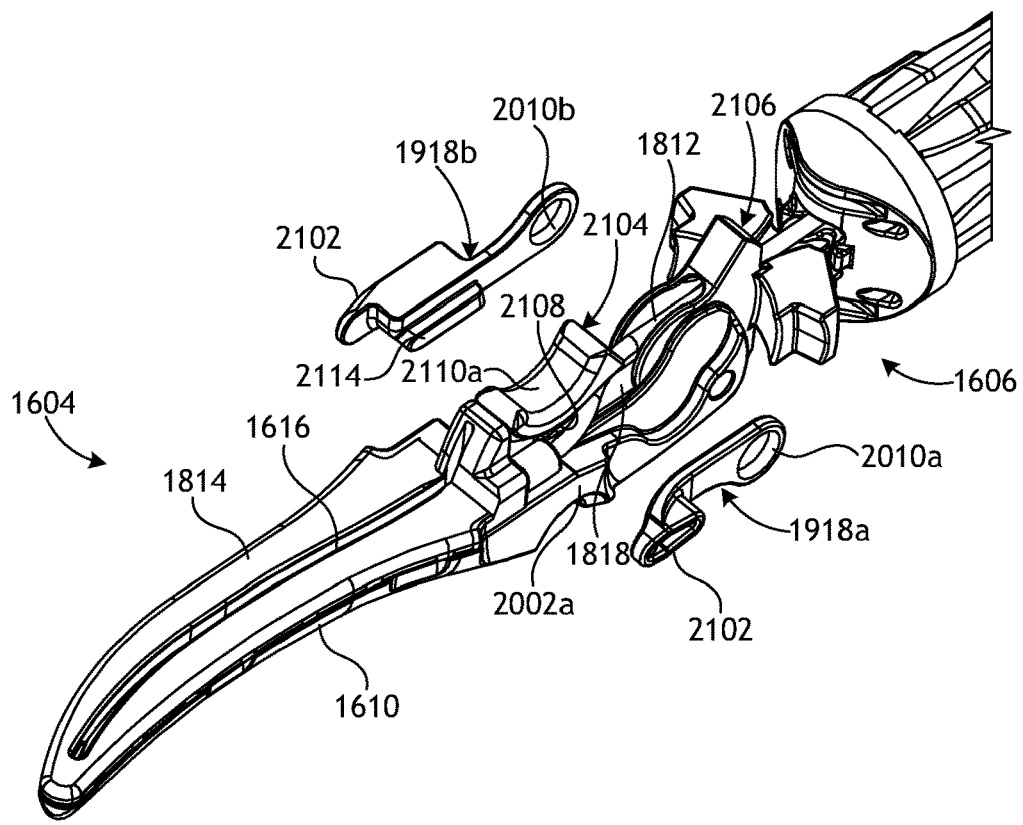
FIGS. 21A and 21B are additional isometric, partially exploded views of the end effector of FIG. 18 from the right and left vantage points.
Figure 21B:
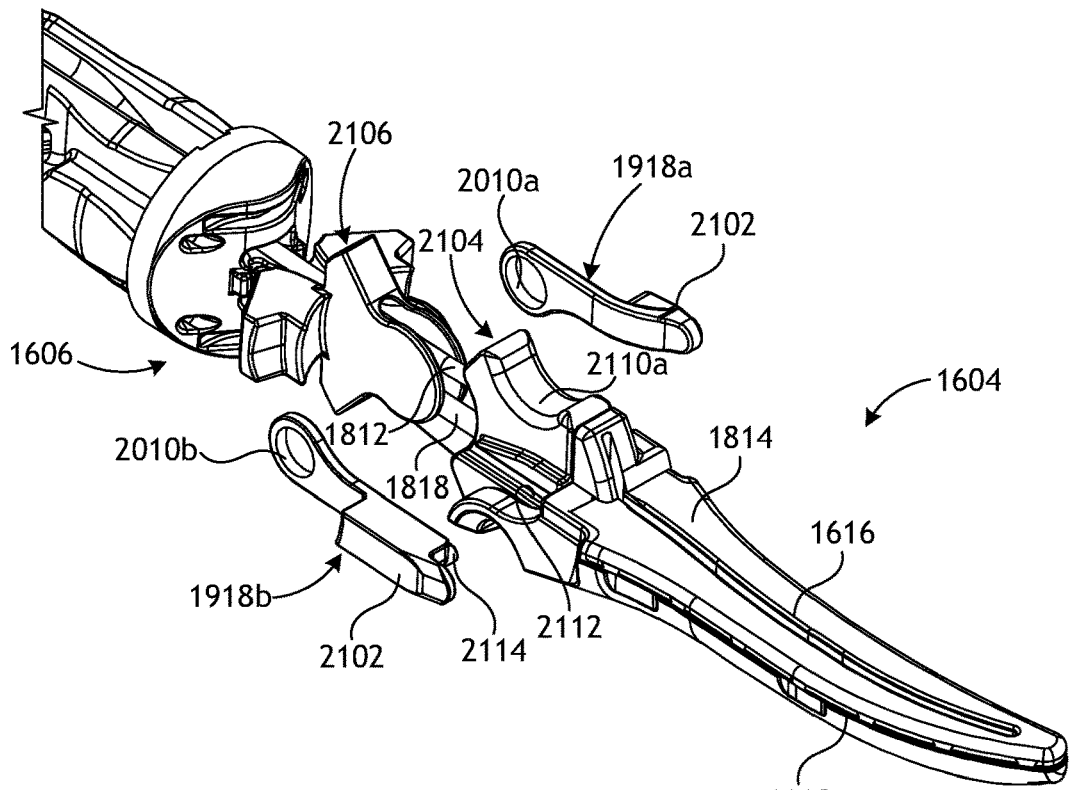

FIGS. 21A and 21B are additional isometric, partially exploded views of the end effector 1604 of FIG. 18 from the right and left vantage points, respectively. In FIGS. 21A-21B, the distal clevis 1802a, the linkage 1804 (FIGS. 19A-19B), the drive members 1808a-d (FIGS. 20A-20B), the pulleys 1806a,b (FIGS. 20A-20B), and the first or "upper" jaw 1612 are all omitted for simplicity. The first and second alignment arms 1918a,b are shown in FIGS. 21A-21B exploded laterally from the remaining portions of the end effector 1604 and the wrist 1606. As mentioned above, however, only one of the alignment arms 1918a,b need be included, without departing from the scope of the disclosure.

In some embodiments, as illustrated, each alignment arm 1918a,b may provide or otherwise define an alignment head 2102 configured or otherwise sized to be received within the corresponding and adjacent slot 1920a,b (FIGS. 19A-19B) defined in the linkage 1804 (FIGS. 19A-19B). The alignment head 2102 may be provided at or near the distal end of each alignment arm 1918a,b, or may otherwise be arranged at any location along the alignment arm 1918a,b and distal to the arm apertures 2010a,b.

In the illustrated embodiment, the wrist 1606 may further include a distal wedge 2104 and a mid-articulation insert 2106 arranged in series and positioned in the central portion or middle of the wrist 1606. The distal wedge 2104 may be arranged between the electrode 1814 and the distal clevis 1802a (FIGS. 19A-19B) and generally arranged within the linkage 1804 (FIGS. 18 and 19A-19B), and the mid-articulation insert 2106 may be generally arranged within the distal clevis 1802a (FIGS. 18 and 19A-19B). The distal wedge 2104 and the mid-articulation insert 2106 may be positioned between (interpose) the first and second jaw extensions 2002a,b of the jaws 1610, 1612 (only the first jaw extension 2002a of the lower jaw 1610 depicted in FIGS. 21A-21B). The distal wedge 2104 and mid-articulation insert 2106 may act to guide the jaw extensions 2002a,b in planar rotation as the jaws 1610, 1612 open, close, and articulate in pitch.

The distal wedge 2104 may be made of a variety of rigid materials including, but not limited to, a metal, a cast metal alloy, a wrought metal, a polymer composite, a ceramic, a negative-index metamaterial (NIM), a metal injection molding (MIM), a reinforced plastic or thermoplastic, (e.g., nylon, polyetherimide or Ultem®, polyether ether ketone or PEEK, etc.), or any combination thereof. In some embodiments, the reinforced plastics or thermoplastics may be carbon or glass filled.

In some embodiments, the distal wedge 2104 may receive and help guide the knife (not shown) to the jaws 1610, 1612. More specifically, the distal wedge 2104 may define a knife cavity (not shown) through which the knife and the drive rod 1818 are able to extend to move the knife into and along the guide track 1616. Upon firing the end effector 1604, the drive rod 1818 is moved (urged) distally, which correspondingly moves the knife out of the distal wedge 2104 and into the guide track 1616. After firing is complete, the drive rod 1818 is retracted proximally, which pulls the knife proximally and back into distal wedge 2104 until it is desired to again fire the end effector 1604.

In some embodiments, the distal wedge 2104 may also receive and help guide the electrical conductor 1812 to the jaws 1610, 1612 and, more particularly, to the electrode 1814 to provide an electrical current generated by at least one electrosurgical generator in electrical communication with the handle 1614 (FIGS. 16 and 17). The distal wedge 2104 may also be configured to protect the electrical conductor 1812 from damage and manage slack in the electrical conductor 1812 while the end effector 1604 and the wrist 1606 to operate. More specifically, the distal wedge 2104 may be designed to guide the electrical conductor 1812 to ensure that it is isolated from moving parts and/or mechanisms of the end effector 1604 or the wrist 1606, which may inadvertently abrade or damage the electrical conductor 1812 and thereby potentially result in arcing or shorting. Example moving parts and/or mechanisms of the end effector 1604 or the wrist 1606 include the knife rod 1818, the clevises 1802a,b, and the articulation arms 1918a,b, all of which could inadvertently contact and damage the electrical conductor 1812 during operation if not properly protected by the distal wedge 2104.

To guide and protect the electrical conductor 1812 from damage, the distal wedge 2104 may provide or otherwise define one or more conductor conduits 2108 (one visible in FIG. 21A) configured to receive and guide the electrical conductor 1812 to the electrode 1814. The conductor conduit(s) 2108 may pass through, around, above, below, or on one or both sides of the distal wedge 2104, or any combination thereof. In some embodiments, the conductor conduit 2108 may define or otherwise provide one or more vertical and/or horizontal curves, undulations, or direction changes that alter the course or pathway of the conductor conduit 2108 and thereby change the course of the electrical conductor 1812 received within the conductor conduit 2108.

The distal wedge 2104 may further provide or otherwise define one or more arcuate surfaces, shown as a first or "upper" arcuate surface 2110a and a second or "lower"

arcuate surface 2110*b* (not visible in FIGS. 21A-21B). As illustrated, the arcuate surfaces 2110*a,b* may comprise concave surfaces, and may be configured to receive and engage corresponding curved (convex) portions of the jaws 1610, 1612. As described in more detail below, the arcuate surfaces 2110*a,b* may operate as camming surfaces for the jaws 1610, 1612 as they open and close.

In some embodiments, as illustrated, a channel 2112 (FIG. 21B) may be provided or otherwise defined on one or both lateral sides of the distal wedge 2104 and may be configured to receive and slidably mate with a corresponding projection 2114 provided by an adjacent alignment arm 1918*a,b*. In the illustrated embodiment, the channel 2112 is provided on only one lateral side of the distal wedge 2104 and is configured to receive and slidably mate with a projection 2114 provided by the second alignment arm 1918*b*. In other embodiments, however, channels 2112 could alternatively be provided on both lateral sides of the distal wedge 2104 and configured to mate with adjacent projections 2114 provided by each alignment arm 1918*a,b*, without departing from the scope of the disclosure.

As illustrated, the projection 2114 may be provided on one lateral side of the alignment arm 1918*b* to slidably mate with the channel 2112, while the alignment head 2102 may be provided on the opposing lateral side of the alignment arm 1918*b* to slidably mate with the second slot 1920*b* (FIG. 19A). In some embodiments, the channel 2112 may extend distally and proximally such that the direction or axis of the channel 2112 is generally parallel to the longitudinal axis A2 (FIGS. 19A-19B) of the end effector 1604. In other embodiments, however, the channel 2112 may be arcuate or otherwise non-straight, without departing from the scope of the disclosure. In such embodiments, for example, both alignment arms 1918*a,b* may be used with pin-in-slot arrangements on each side. Depending on the specifics of the arrangement, a coupled motion between jaw closure and pitch cold be achieved, and this type of coupling could result in a predefined end effector rotation during jaw closure, coupled with robotic arm motion can create the user perceived effect of the bottom jaw remaining stationary against tissue while the top jaw completes the clamping motion. As discussed in more detail below, slidably mating the projection 2114 within the channel 2112 may help rotationally constrain the distal wedge 2104 to the alignment arm 1918*b*, which may help reduce backlash in the jaws 1610, 1612.

While FIGS. 21A-21B depict the channel 2112 as being provided on the distal wedge 2104 and the projection 2114 as being provided on the alignment arm 1918*b*, the component features may be switched, without departing from the scope of the disclosure. More specifically, it is contemplated herein that the channel 2112 may alternatively be provided on the alignment arm 1918*b* and the projection 2114 may alternatively be provided on the distal wedge 2104.

Figure 22:
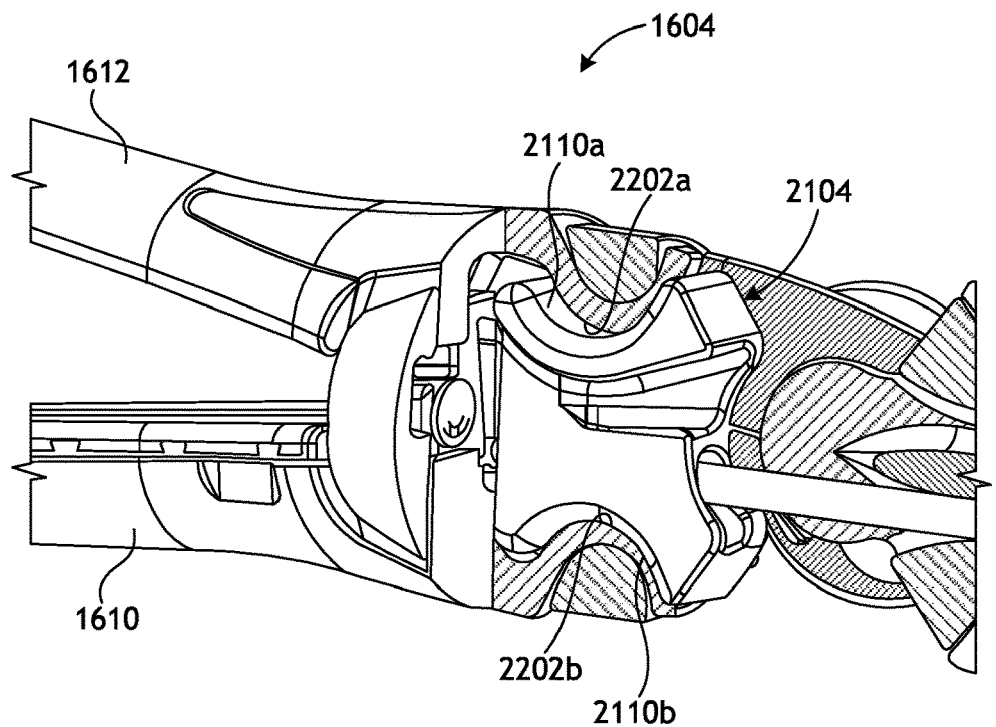
FIG. 22 is an enlarged, partial cross-sectional side view of the end effector, according to one or more embodiments.

FIG. 22 is an enlarged, partial cross-sectional side view of the end effector 1604, according to one or more embodiments. As mentioned above, the distal wedge 2104 may provide upper and lower arcuate (concave) surfaces 2110*a,b* configured to receive and engage corresponding curved (convex) portions of the jaws 1610, 1612. More specifically, the upper jaw 1612 may provide or define a first or "upper" journal 2202*a* configured to engage the upper arcuate surface 2110*a*, and the lower jaw 1610 may provide or define a second or "lower" journal 2202*b* configured to engage the lower arcuate surface 2110*b*. Engagement between the opposing arcuate surfaces 2110*a,b* and journals 2202*a,b*, respectively, provides or facilitates the jaw pivot point discussed herein, where the jaws 1610, 1612 pivot between open and closed positions. As the jaws 1610, 1612 move between the open and closed positions, the opposing arcuate surfaces 2110*a,b* and journals 2202*a,b* act in sliding engagement as opposing camming surfaces.

The arcuate surfaces 2110*a,b* of the distal wedge 2104 may prove advantageous in touch and spread dissection operations, where a user opens the jaws 1610, 1612 to move tissue. In such operations, a load is applied on the top or bottom of the jaws 1610, 1612 and this load is transferred to the distal wedge 2104 at the corresponding arcuate surface 2110*a,b*. Furthermore, the distal wedge 2104 acts between the jaws 1610, 1612 during spread dissection, where the jaws 1610, 1612 are placed between tissue planes or through an aperture in tissue, and then opened to separate tissue and such loads are transferred to the arcuate surfaces 2110*a,b* and borne by the distal wedge 2104. Accordingly, the arcuate surfaces 2110*a,b* help support the jaws 1610, 1612 and bear loading forces that are required to move or spread tissue.

The jaws 1610, 1612 are depicted in FIG. 22 in an open position. When in this orientation and brought into contact with an adjacent structure during operation (e.g., a vessel, an organ, tissue, etc.), the jaws 1610, 1612 will oftentimes move (shift) until clearance between structural components of the end effector 1604 is taken up and the end effector 1604 eventually stiffens. The effect of such clearance between adjacent structural components of the end effector 1604 manifests as a lack of jaw stiffness, which is often referred to as jaw backlash. Those skilled in the art will readily appreciate that jaw backlash can reduce the effectiveness of surgical tasks, such as blunt dissection and otomy creation in tissue.

One prevalent cause of jaw backlash results as the distal wedge 2104 moves, shifts, or rotates when acted upon by movement of the jaws 1610, 1612 at the upper and lower journals 2202*a,b*. To the extent permitted by component clearances, the jaws 1610, 1612 can shear distal to proximal as the distal wedge 2104 rotates or shifts beneath forces transferred from the journals 2202*a,b*. This jaw motion allows play or backlash to occur in the pitch axis until clearances are taken up. As described here "shearing" is the term given to the top jaw translating distally in the direction of the shaft axis, while the lower jaw simultaneously translates proximally, and vise versa. This jaw motion allows play or backlash to occur in the pitch axis until clearances are taken up. According to embodiments of the present disclosure, the sliding and mated engagement between the projection 2114 (FIGS. 21A-21B) and the channel 2112 (FIGS. 21A-21B) provided on the distal wedge 2104 may help stabilize and rotationally constrain the distal wedge 2104, which may help reduce resulting backlash in the jaws 1610, 1612.

Figure 23:
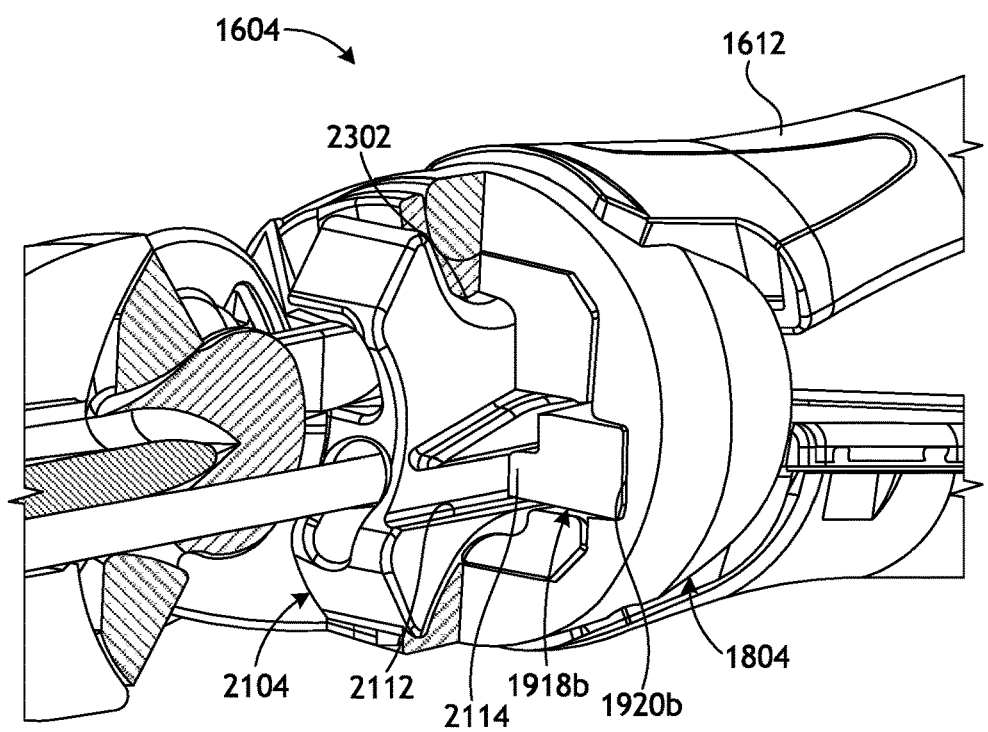
FIG. 23 is another enlarged, partial cross-sectional side view of the end effector, according to one or more embodiments.

FIG. 23 is another enlarged, partial cross-sectional side view of the end effector 1604, according to one or more embodiments. As illustrated, the projection 2114 provided by the second alignment arm 1918*b* is received within the channel 2112 defined or otherwise provided on the lateral side of the distal wedge 2104. Slidably receiving the projection 2114 within the channel 2112 helps to rotationally constrain the distal wedge 2104 to the alignment arm 1918*b*, and, as discussed above, the alignment arm 1918*a* is configured to translate within the slot 1920*b* defined in the linkage 1804. Consequently, receiving the projection 2114 within the channel 2112 effectively constrains the distal wedge 2104 to the linkage 1804, and thereby limits unwanted jaw rotation with respect to the distal articulation joint; i.e., reduction in jaw backlash.

In some embodiments, the structure that helps define the channel 2112 may further provide or otherwise define an upper surface 2302 engageable with a portion of the upper jaw 1612. As illustrated, the upper surface 2302 may be ramped, angled, or otherwise arcuate to help support the upper jaw 1612 and further provide clearance for the upper jaw 1612 to move between the open and closed positions.

Embodiments disclosed herein include:

A. A robotic surgical tool includes an elongate shaft, an end effector arranged at a distal end of the shaft and including opposing first and second jaws, and an articulable wrist interposing the end effector and the distal end of the shaft, the wrist including a linkage mounted to the first and second jaws and defining a slot, a distal wedge arranged at least partially within the linkage, an alignment arm interposing the linkage and the distal wedge and providing an alignment head receivable within the slot, a channel provided on one of the distal wedge or the alignment arm, and a projection provided on the other of the distal wedge or the alignment arm and receivable within the channel, wherein the alignment head is translatable within the slot and the projection is translatable within the channel during operation of the end effector.

B. An end effector for a robotic surgical tool includes opposing first and second jaws, and an articulable wrist operatively coupled to the first and second jaws and including a linkage mounted to the first and second jaws and defining a slot, a distal wedge arranged at least partially within the linkage, an alignment arm interposing the linkage and the distal wedge and providing an alignment head receivable within the slot, a channel provided on one of the distal wedge or the alignment arm, and a projection provided on the other of the distal wedge or the alignment arm and receivable within the channel, wherein the alignment head is translatable within the slot and the projection is translatable within the channel during operation of the end effector.

C. A method of operating a robotic surgical tool includes locating a robotic surgical tool adjacent a patient, the robotic surgical tool having an elongate shaft, an end effector arranged at a distal end of the shaft and including opposing first and second jaws, and an articulable wrist that interposes the end effector and the distal end, the wrist including, a linkage mounted to the first and second jaws and defining a slot, a distal wedge arranged at least partially within the linkage, an alignment arm interposing the linkage and the distal wedge and providing an alignment head receivable within the slot, a channel provided on one of the distal wedge or the alignment arm, and a projection provided on the other of the distal wedge or the alignment arm and receivable within the channel. The method further including operating the end effector or the wrist, stabilizing the distal wedge with the projection received within the channel as the end effector or the wrist operate, and reducing backlash in the end effector with the alignment head received within the slot as the end effector or the wrist operate.

Each of embodiments A, B, and C may have one or more of the following additional elements in any combination: Element 1: wherein the first jaw provides a first jaw extension and the second jaw provides a second jaw extension, the articulable wrist further including a distal clevis, and first and second pulleys rotatably mounted to the distal clevis at a pivot axis, the first jaw extension being pinned to the first pulley and the second jaw extension being pinned to the second pulley, wherein the alignment arm is rotatably mounted to the first pulley at the pivot axis. Element 2: wherein the distal wedge is positioned between the first and second jaw extensions. Element 3: wherein the distal wedge defines upper and lower arcuate surfaces engageable with upper and lower journals, respectively, provided by the first and second jaws. Element 4: wherein the first and second jaw extensions are pinned to the first and second pulleys, respectively, eccentric to the pivot axis. Element 5: further comprising an electrical conductor extending through the wrist and to an electrode located at the end effector, wherein the distal wedge guides the electrical conductor to the electrode. Element 6: further comprising a knife rod extendable through the central portion of the wrist and terminating at a knife, the knife rod and the knife being translatable through the distal wedge. Element 7: wherein the slot is a first slot, the alignment arm is a first alignment arm, and the alignment head is a first alignment head, the articulable wrist further including a second alignment arm rotatably mounted to the second pulley at the pivot axis and providing a second alignment head translatable within a second slot defined in the linkage, wherein the second slot extends parallel to a longitudinal axis of the end effector. Element 8: further comprising a handle through which the shaft is extendable, the handle being matable with an instrument driver arranged at an end of a robotic arm, and a plurality of drive members extending along the shaft and terminating at the first and second pulleys, wherein the plurality of drive members are antagonistically operable via the handle to open and close the first and second jaws and articulate the end effector in pitch and yaw. Element 9: wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, and any combination thereof.

Element 10: wherein the first jaw provides a first jaw extension and the second jaw provides a second jaw extension, the articulable wrist further including a distal clevis, and first and second pulleys rotatably mounted to the distal clevis at a pivot axis, the first jaw extension being pinned to the first pulley and the second jaw extension being pinned to the second pulley, wherein the alignment arm is rotatably mounted to the first pulley at the pivot axis. Element 11: wherein the distal wedge is positioned between the first and second jaw extensions. Element 12: wherein the distal wedge defines upper and lower arcuate surfaces engageable with upper and lower journals, respectively, provided by the first and second jaws. Element 13: wherein the projection is provided on a first lateral side of the alignment arm and the alignment head is provided on a second lateral side of the alignment arm. Element 14: wherein the channel extends distally and proximally and parallel to a longitudinal axis of the end effector. Element 15: wherein the channel defines a ramped upper surface engageable with a portion of the first jaw.

Element 16: wherein the channel extends parallel to a longitudinal axis of the end effector, and wherein stabilizing the distal wedge with the projection received within the channel comprises translating the projection within the channel as the first and second jaws open and close. Element 17: wherein the first jaw provides a first jaw extension, the second jaw provides a second jaw extension, and the articulable wrist further includes a distal clevis and first and second pulleys rotatably mounted to the distal clevis at a pivot axis, the first jaw extension being pinned to the first pulley, the second jaw extension being pinned to the second pulley, and the alignment arm being rotatably mounted to the first pulley at the pivot axis, the method further comprising, actuating the first and second pulleys to open or close the first and second jaws, and preventing the first and second jaws from rotating in pitch or out of alignment with each other with the alignment head received within the slot.

By way of non-limiting example, exemplary combinations applicable to A, B, and C include: Element 1 with Element 2; and Element 10 with Element 11.

3. Implementing Systems and Terminology

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112 (f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
   an elongate shaft;
   an end effector arranged at a distal end of the shaft and including opposing first and second jaws; and
   an articulable wrist interposing the end effector and the distal end of the shaft, the wrist including:
      a linkage mounted to the first and second jaws and defining a slot;
      a distal wedge arranged at least partially within the linkage;
      an alignment arm laterally interposing the linkage and the distal wedge and providing an alignment head receivable within the slot;
      a channel provided on one of the distal wedge or the alignment arm; and
      a projection provided on the other of the distal wedge or the alignment arm and receivable within the channel,
   wherein the alignment head is translatable within the slot and the projection is translatable within the channel during operation of the end effector.

2. The robotic surgical tool of claim 1, wherein the first jaw provides a first jaw extension and the second jaw provides a second jaw extension, the articulable wrist further including:
   a distal clevis; and
   first and second pulleys rotatably mounted to the distal clevis at a pivot axis, the first jaw extension being pinned to the first pulley and the second jaw extension being pinned to the second pulley,
   wherein the alignment arm is rotatably mounted to the first pulley at the pivot axis.

3. The robotic surgical tool of claim 2, wherein the distal wedge is positioned between the first and second jaw extensions.

4. The robotic surgical tool of claim 1, wherein the distal wedge defines upper and lower arcuate surfaces engageable with upper and lower journals, respectively, provided by the first and second jaws.

5. The robotic surgical tool of claim 1, wherein the first and second jaw extensions are pinned to the first and second pulleys, respectively, eccentric to the pivot axis.

6. The robotic surgical tool of claim 1, further comprising an electrical conductor extending through the wrist and to an electrode located at the end effector, wherein the distal wedge guides the electrical conductor to the electrode.

7. The robotic surgical tool of claim 1, further comprising a knife rod extendable through the central portion of the wrist and translatable through the distal wedge.

8. The robotic surgical tool of claim 1, wherein the slot is a first slot, the alignment arm is a first alignment arm, and the alignment head is a first alignment head, the articulable wrist further including:
   a second alignment arm rotatably mounted to the second pulley at the pivot axis and providing a second alignment head translatable within a second slot defined in the linkage, wherein the second slot extends parallel to a longitudinal axis of the end effector.

9. The robotic surgical tool of claim 1, further comprising:
   a handle through which the shaft is extendable, the handle being matable with an instrument driver arranged at an end of a robotic arm; and
   a plurality of drive members extending along the shaft and terminating at the first and second pulleys, wherein the plurality of drive members are antagonistically operable via the handle to open and close the first and second jaws and articulate the end effector in pitch and yaw.

10. The robotic surgical tool of claim 1, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, and any combination thereof.

11. An end effector for a robotic surgical tool, comprising:
opposing first and second jaws; and
an articulable wrist operatively coupled to the first and second jaws and including:
  a linkage mounted to the first and second jaws and defining a slot;
  a distal wedge arranged at least partially within the linkage;
  an alignment arm laterally interposing the linkage and the distal wedge and providing an alignment head receivable within the slot;
  a channel provided on one of the distal wedge or the alignment arm; and
  a projection provided on the other of the distal wedge or the alignment arm and receivable within the channel,
wherein the alignment head is translatable within the slot and the projection is translatable within the channel during operation of the end effector.

12. The end effector of claim 11, wherein the first jaw provides a first jaw extension and the second jaw provides a second jaw extension, the articulable wrist further including:
a distal clevis; and
first and second pulleys rotatably mounted to the distal clevis at a pivot axis, the first jaw extension being pinned to the first pulley and the second jaw extension being pinned to the second pulley,
wherein the alignment arm is rotatably mounted to the first pulley at the pivot axis.

13. The end effector of claim 12, wherein the distal wedge is positioned between the first and second jaw extensions.

14. The end effector of claim 11, wherein the distal wedge defines upper and lower arcuate surfaces engageable with upper and lower journals, respectively, provided by the first and second jaws.

15. The end effector of claim 11, wherein the projection is provided on a first lateral side of the alignment arm and the alignment head is provided on a second lateral side of the alignment arm.

16. The end effector of claim 11, wherein the channel extends distally and proximally and parallel to a longitudinal axis of the end effector.

17. The end effector of claim 11, wherein the channel defines a ramped upper surface engageable with a portion of the first jaw.

18. A method of operating a robotic surgical tool, comprising:
locating a robotic surgical tool adjacent a patient, the robotic surgical tool having an elongate shaft, an end effector arranged at a distal end of the shaft and including opposing first and second jaws, and an articulable wrist that interposes the end effector and the distal end, the wrist including:
  a linkage mounted to the first and second jaws defining a slot;
  a distal wedge arranged at least partially within the linkage;
  an alignment arm laterally interposing the linkage and the distal wedge and providing an alignment head receivable within the slot;
  a channel provided on one of the distal wedge or the alignment arm; and
  a projection provided on the other of the distal wedge or the alignment arm and receivable within the channel;
operating the end effector or the wrist;
stabilizing the distal wedge with the projection received within the channel as the end effector or the wrist operate; and
reducing backlash in the end effector with the alignment head received within the slot as the end effector or the wrist operate.

19. The method of claim 18, wherein the channel extends parallel to a longitudinal axis of the end effector, and wherein stabilizing the distal wedge with the projection received within the channel comprises translating the projection within the channel as the first and second jaws open and close.

20. The method of claim 18, wherein the first jaw provides a first jaw extension, the second jaw provides a second jaw extension, and the articulable wrist further includes a distal clevis and first and second pulleys rotatably mounted to the distal clevis at a pivot axis, the first jaw extension being pinned to the first pulley, the second jaw extension being pinned to the second pulley, and the alignment arm being rotatably mounted to the first pulley at the pivot axis, the method further comprising,
actuating the first and second pulleys to open or close the first and second jaws; and
preventing the first and second jaws from rotating in pitch or out of alignment with each other with the alignment head received within the slot.

* * * * *